United States Patent
Mun et al.

(10) Patent No.: US 11,512,086 B2
(45) Date of Patent: Nov. 29, 2022

(54) COMPOUND FOR ORGANIC ELECTRICAL ELEMENT, ORGANIC ELECTRICAL ELEMENT USING COMPOUND, AND ELECTRONIC DEVICE THEREFOR

(71) Applicant: DUK SAN NEOLUX CO., LTD., Cheonan-si (KR)

(72) Inventors: Soung Yun Mun, Cheonan-si (KR); Sun Hee Lee, Hwaseong-si (KR); Seung Won Yeo, Daejeon (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 1074 days.

(21) Appl. No.: 15/748,887

(22) PCT Filed: Jul. 19, 2016

(86) PCT No.: PCT/KR2016/007866
§ 371 (c)(1),
(2) Date: Jan. 30, 2018

(87) PCT Pub. No.: WO2017/022983
PCT Pub. Date: Feb. 9, 2017

(65) Prior Publication Data
US 2018/0222910 A1    Aug. 9, 2018

(30) Foreign Application Priority Data

Aug. 3, 2015 (KR) .......... 10-2015-0109540

(51) Int. Cl.
| | | |
|---|---|---|
| H01L 51/54 | (2006.01) |
| C07D 487/04 | (2006.01) |
| C09K 11/06 | (2006.01) |
| C07D 409/04 | (2006.01) |
| C07D 405/04 | (2006.01) |
| H01L 51/00 | (2006.01) |
| C07D 405/14 | (2006.01) |
| H01L 51/50 | (2006.01) |
| H01L 51/56 | (2006.01) |

(52) U.S. Cl.
CPC ......... *C07D 487/04* (2013.01); *C07D 405/04* (2013.01); *C07D 405/14* (2013.01); *C07D 409/04* (2013.01); *C09K 11/06* (2013.01); *H01L 51/0054* (2013.01); *H01L 51/0055* (2013.01); *H01L 51/0058* (2013.01); *H01L 51/0067* (2013.01); *H01L 51/0072* (2013.01); *H01L 51/0073* (2013.01); *H01L 51/0074* (2013.01); *H01L 51/5012* (2013.01); *H01L 51/5016* (2013.01); *H01L 51/56* (2013.01)

(58) Field of Classification Search
None
See application file for complete search history.

(56) References Cited

U.S. PATENT DOCUMENTS

2010/0051928 A1* 3/2010 Fukuzaki .............. C07F 9/6561
257/40
2012/0138914 A1* 6/2012 Kawamura .......... C07D 333/74
257/40

FOREIGN PATENT DOCUMENTS

| CN | 104119347 A | | 10/2014 |
| JP | 2012-191031 A | | 10/2012 |
| JP | 2012191031 A | * | 10/2012 |
| JP | 2013-147481 A | | 8/2013 |
| JP | 2013-183011 A | | 9/2013 |
| JP | 2014-73965 A | | 4/2014 |
| WO | 2015/022987 A1 | | 2/2015 |

OTHER PUBLICATIONS

Machine translation of JP2012-191031. (Year: 2012).*
Chinese Office Action for corresponding CN 201680045509.5, dated Nov. 27, 2020, 6 pages.

* cited by examiner

*Primary Examiner* — Andrew K Bohaty
(74) *Attorney, Agent, or Firm* — Vorys, Sater, Seymour and Pease LLP; Mih Suhn Koh

(57) ABSTRACT

Provided is a novel compound capable of improving the light emitting efficiency, stability and life span of a device, and an organic electric element and an electronic device using the same.

11 Claims, 1 Drawing Sheet

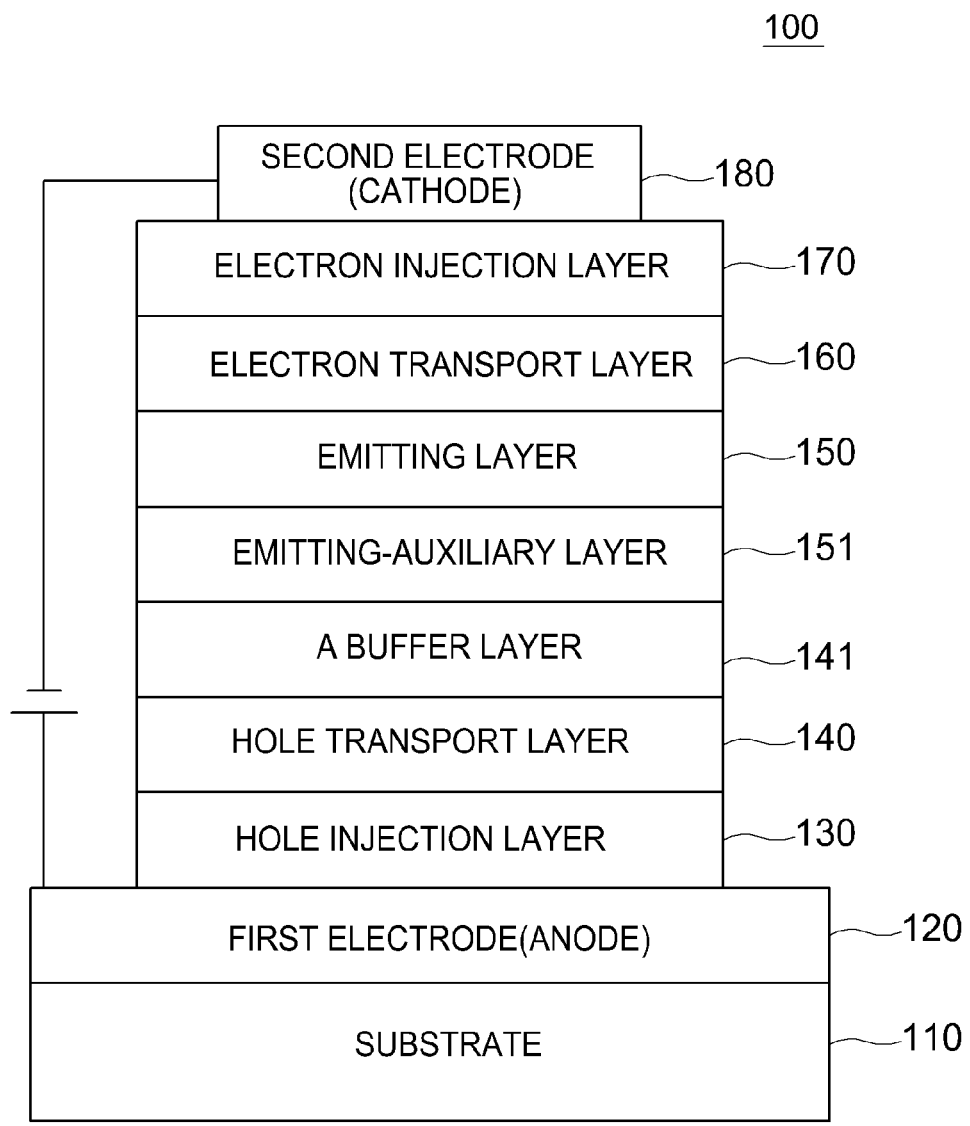

COMPOUND FOR ORGANIC ELECTRICAL ELEMENT, ORGANIC ELECTRICAL ELEMENT USING COMPOUND, AND ELECTRONIC DEVICE THEREFOR

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

And the light emitting material may be classified into a polymer type and a low molecular type depending on the molecular weight, and into a fluorescent material derived from the singlet excited state of electrons and a phosphorescent material derived from the triplet excited state of electrons depending on the light emitting mechanism. Further, the light emitting material can be classified into blue, green, and red light emitting materials and yellow and orange light emitting materials necessary for realizing better natural color depending on the luminescent color.

Meanwhile, when only one material is used as a light emitting material, there arises a problem that the maximum light emission wavelength shifts to a long wavelength due to intermolecular interaction, the color purity drops, or the efficiency of the device decreases due to the light emission attenuation effect, therefore a host/dopant system can be used as a light emitting material in order to increase luminous efficiency through increase of color purity and energy transfer. When the small amount of dopant having a smaller energy band gap than the host forming the emitting layer is mixed on the emitting layer, the excitons generated in the emitting layer are transported to the dopant to emit light with high efficiency. At this time, since the wavelength of the host is shifted to the wavelength band of the dopant, light of a desired wavelength can be obtained depending on the type of the dopant used.

Currently, the portable display market is growing in size as a large-area display, which requires more power than the power consumption required by existing portable displays. Therefore, power consumption is a very important factor for portable displays, which have a limited power source, such as a battery, and efficiency and lifetime issues must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase. However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time. Therefore, it is necessary to develop a light emitting material having a high thermal stability and achieving a charge balance in the emitting layer efficiently.

That is, in order to sufficiently exhibit the excellent characteristics of the organic electric element, a material for forming an organic material layer in an element such as a hole injection material, a hole transport material, a light emitting material, an electron transport material, an electron injection material, an emitting-auxiliary layer material, and the like should be supported by stable and efficient materials. However, such a stable and efficient organic material layer material for an organic electric element has not been sufficiently developed yet. Therefore, development of new materials is continuously required, and especially development of host materials for the emitting layer is urgently required.

Related prior art documents include the following documents.

(Patent Document 1) U.S. Pat. No. 6,596,415 B2
(Patent Document 2) U.S. Pat. No. 6,465,115 B2

DETAILED DESCRIPTION OF THE INVENTION

Summary

The present invention provides a compound capable of improving a high luminous efficiency, a low driving voltage, a high heat resistance, a color purity and a lifetime of a device, an organic electric element using the same, and an electronic device thereof.

Technical Solution

The present invention provides a compound represented by the following formula.

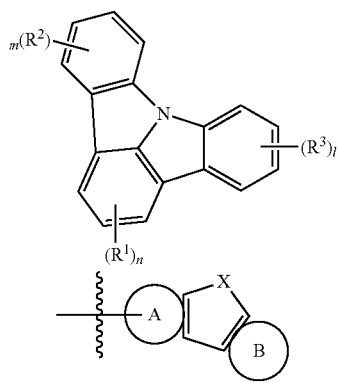

In another aspect, the present invention provides an organic electronic element using the compound represented by the above formula and an electronic device thereof.

Effects of the Invention

By using the compound according to the present invention, it is possible to achieve a high luminous efficiency, a low driving voltage, and a high heat resistance of the element, and can greatly improve the color purity and lifetime of the element.

BRIEF DESCRIPTION OF THE DRAWINGS

The FIGURE illustrates an example of an organic electric element according to the present invention.

100: organic electric element,  110: substrate
120: the first electrode(anode),  130: the hole injection layer
140: the hole transport layer,  141: a buffer layer
150: the emitting layer,  151: the emitting auxiliary layer
160: the electron transport layer,  170: the electron injection layer
180: the second electrode(cathode)

DETAILED DESCRIPTION

Hereinafter, some embodiments of the present invention will be described in detail.

It is to be noted that, in adding reference numerals to the constituent elements of the drawings, the same constituent elements are denoted by the same reference numerals whenever possible, even if they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component. Also, when an element such as a layer, film, region, plate, or the like is referred to as being "over" or "on" another element, it should be understood that this may include not only the case "directly above" another element but also the case where there is another element in between. On the contrary, when an element is referred to as being "directly on" another element, it should be understood that there is no other element in between.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "fluorenyl group" or "fluorenylene group", as used herein, means a monovalent or divalent functional group in which, in the following structures, R, R' and R" are both hydrogen, and "substituted fluorenyl group" or "substituted fluorenylene group" means that at least one of substituents R, R', R "is a substituent other than hydrogen, and R and R' are bonded to each other to form a spiro compound together with the carbon to which they are bonded.

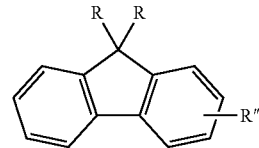

Unless otherwise stated, the term "aryl group" or "arylene group", as used herein, has 6 to 60 carbon atoms, but is not limited thereto. In the present invention, the aryl group or the arylene group includes a single ring type, a ring bonding group, a plurality of bonded ring systems, a spiro compound, and the like.

The term "heterocyclic group", as used herein, includes not only aromatic rings such as "heteroaryl groups" or "heteroarylene groups" but also nonaromatic rings and, unless otherwise stated, means a ring a C2 to C60 aryl containing one or more of hetero atoms or arylene group, but is not limited thereto. Unless otherwise stated, the term "heteroatom", as used herein, represents at least one of N, O, S, P, or Si, and the heterocyclic group means a single ring including a hetero atom, a ring junction, a plurality of ring systems bonded together, a spiro compound, and the like.

Also, the term "heterocyclic group" may include a ring containing $SO_2$ instead of carbon consisting of cycle. For example, "heterocyclic group" includes compound below.

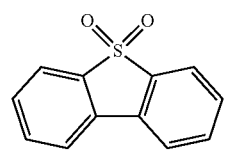 [SMILES: O=S1(=O)c2ccccc2-c2ccccc21]

The term "ring", as used herein, includes monocyclic and polycyclic rings, and includes not only hydrocarbon rings but also heterocycles containing at least one heteroatom, including aromatic and non-aromatic rings.

The term "polycyclic", as used herein, includes ring assemblies such as biphenyl, terphenyl, and the like, fused multiple ring systems and spiro compounds, and includes not only aromatic but also non-aromatic, and includes a heterocycle including at least one heteroatom as well as a hydrocarbon ring.

The term "ring assemblies", as used herein, means that two or more ring systems (a single ring or a fused ring system) are directly linked to each other through a single bond or a double bond and that the number of direct connections between such rings is one less than the total number of rings in the compound. The ring assemblies may be directly linked to each other through a single bond or a double bond of the same or different ring systems.

The term "fused ring system", as used herein, means a fused ring form sharing at least two atoms, and includes a form in which two or more hydrocarbons ring system is fused, and a form in which at least one heterocyclic system containing at least one hetero atom is fused. These fused multiple ring systems may be aromatic rings, heteroaromatic rings, aliphatic rings or a combination of these rings.

The term "spiro compound", as used herein, has a "spiro union", and the spiro union means a link consisting of two rings sharing only one atom. At this time, atoms shared in the two rings are referred to as 'spiro atoms' and these compounds are called 'monospiro-', 'di-spiro-', and 'tri-spiro' compounds, depending on the number of atoms in a compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

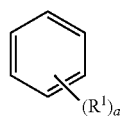

wherein, when a is an integer of zero, the substituent $R^1$ is absent, when a is an integer of 1, the sole substituent $R^1$ is linked to any one of the carbon constituting the benzene ring, when a is an integer of 2 or 3, they are respectively bonded as follows, in which $R^1$ may be the same as or different from each other, when a is an integer of 4 to 6, it bonds to the carbon of the benzene ring in a similar manner, and the indication of the hydrogen bonded to the carbon forming the benzene ring is omitted.

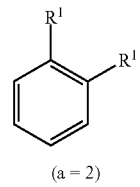 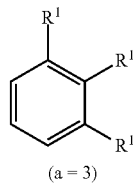

(a = 2)  (a = 3)

The FIGURE is an illustration of an organic electric element according to an embodiment of the present invention.

Referring to the FIGURE, the organic electric element (100) according to the present invention includes a first electrode (120) formed on a substrate (110), a second electrode (180), and an organic material layer between the first electrode (120) and the second electrode (180), which contains the compound represented by Formula 1. Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, at least one of these layers may be omitted, or a hole blocking layer, an electron blocking layer, an emitting-auxiliary layer (151), a buffer layer (141), etc. may be further included, and the electron transport layer (160) and the like may serve as a hole blocking layer.

Although not shown, the organic electric element according to the present invention may further include a protective layer or a capping layer formed on at least one side of the first and second electrodes, which is a side opposite to the organic material layer.

The compound according to the present invention applied to the organic material layer may be used as a material such as a hole injection layer (130), a hole transport layer (140), an electron transport layer (160), an electron injection layer (170), an emitting layer (150), a capping layer, an emitting-auxiliary layer, and the like. As an example, the compound of the present invention can be used as material of the emitting-auxiliary layer (151) and/or the emitting layer (150).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and intrinsic properties of materials (mobility, interfacial properties, etc.) of each organic material layer is achieved, a long life span and high efficiency can be achieved at the same time.

Recently, as described above, in order to solve the emission problem in the hole transport layer of an organic electric element, an emitting-auxiliary layer is preferable formed between the hole transport layer and an emitting layer, and it is necessary to form different emitting-auxiliary layers corresponding to respective emitting layers (R, G, B). Meanwhile, in the case of the emitting-auxiliary layer, mutual relationship between hole transport layer and emitting layer (host) should be figured out. Even if similar cores are used, it will be very difficult to deduce the characteristics if the organic material layer used is different.

Therefore, by forming the emitting layer and/or the emitting-auxiliary layer using the compound of Formula (1) of the present invention, it is possible to simultaneously improve the lifetime and the efficiency of the organic electric element by optimizing the energy level and T1 value between each organic material layer and the intrinsic properties of the material (mobility, interface characteristics).

The organic electric element according to an embodiment of the present invention may be manufactured using various deposition methods. It can be manufactured using a deposition method such as PVD or CVD, for example, the organic electric element may be manufactured by depositing a metal or a conductive metal oxide or a mixture thereof on the substrate (110) to form the anode (120), forming the organic material layer including the hole injection layer (130), the hole transport layer (140), the emitting layer (150), the electron transport layer (160), and the electron injection layer (170) thereon, and then depositing a material, which can be used as the cathode (180), thereon. Further, an emitting-auxiliary layer (151) may be additionally formed between the hole transport layer (140) and the emitting layer (150).

In addition, the organic material layer can be fabricated into a smaller number of layers by using various polymer materials in a solution process or a solvent process such as a spin coating process, a nozzle printing process, an inkjet printing process, a slot coating process, a dip coating process or a roll-to-roll process, a doctor blading process, a screen printing process or heat transfer method etc. Since the organic material layer according to the present invention can be formed by various methods, the scope of the present invention is not limited by the method of forming the organic material layer.

The organic electric element according to an embodiment of the present invention may be a front emission type, a back emission type, or a both-sided emission type, depending on the material used. WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the emitting part of the red (R), green (G) and blue (B), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The organic electric element according to the present invention may be one of an OLED, an organic solar cell, an organic photo conductor, an organic transistor and an element for monochromic or white illumination.

Another embodiment of the present invention may include a display device including the above-described organic electric element of the present invention and an electronic device including a control unit for driving the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, the compound according to one aspect of the present invention will be described.

A compound according to one aspect of the present invention is represented by the following Formula (1).

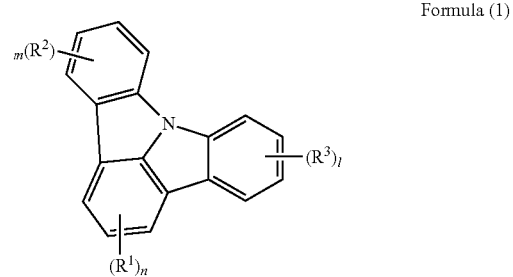

Formula (1)

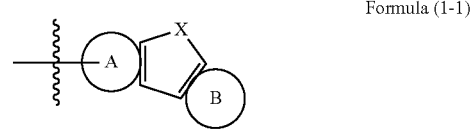

Formula (1-1)

{In Formula (1)

1) m and l are integers of 0 to 4, n is an integer of 0 to 3, and at least one of $R^1$, $R^2$ and $R^3$ is necessarily the above Formula (1-1), and when the Formula (1-1) is unsubstituted, $R^1$, $R^2$ and $R^3$ are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$)(wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P), Or when m, n, and l are two or more, they are the same as or different from each other, or a plurality of $R^1$ or a plurality of $R^2$ or a plurality of $R^3$ may combine to each other to form a ring, 2) In Formula (1-1)

X is selected from the group consisting of O, S, CR'R", wherein R' and R" are independently a $C_1$-$C_{50}$ alkyl group; a $C_6$-$C_{60}$ aryl group; a $C_2$-$C_{60}$ heterocyclic group including at least one hetero atom of O, N, S, Si and P; and may be bonded to each other to form a spiro and the A ring and the B ring are $C_6$-$C_{60}$ aryl group; and at least one is an aryl group of $C_{10}$ or more.

(wherein, the aryl group, heteroaryl group, fluorenyl group, arylene group, heterocyclic group, fused ring group may be further substituted with one or more substituents selected from the group consisting of deuterium; halogen; a silane group; siloxane group; boron group; germanium group; cyano group; nitro group; -L'-N(R$_a$)(R$_b$); a C$_1$-C$_{20}$ alkylthio group; C$_1$-C$_{20}$ alkoxyl group; C$_1$-C$_{20}$ alkyl group; C$_2$-C$_{20}$ alkenyl group; C$_2$-C$_{20}$ alkynyl group; C$_6$-C$_{20}$ aryl group; C$_6$-C$_{20}$ aryl group substituted with deuterium; a fluorenyl group; C$_2$-C$_{20}$ heterocyclic group; C$_3$-C$_{20}$ cycloalkyl group; C$_7$-C$_{20}$ arylalkyl group and C$_8$-C$_{20}$ arylalkenyl group, and also, these substituents may combine each other and form a ring, wherein the term 'ring' means a C$_3$-C$_{60}$ aliphatic ring; or a C$_6$-C$_{60}$ aromatic ring; or a C$_2$-C$_{60}$ heterocyclic ring; or a fused ring formed by the combination of thereof and includes saturated or unsaturated rings.)}

Specifically, the present invention provides a compound wherein the compound represented by Formula (1) is represented by the following Formula (2) or (3).

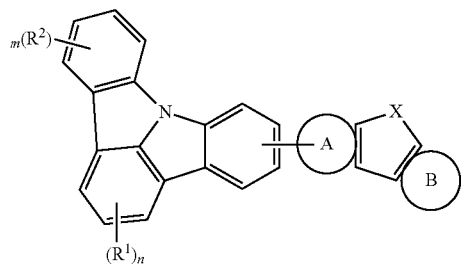

Formula (2)

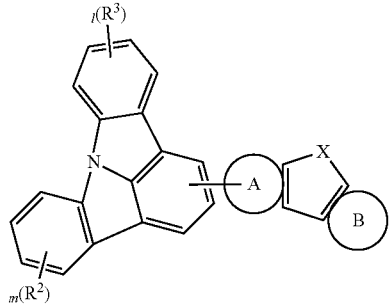

Formula (3)

In Formula (2) or (3), R$^1$, R$^2$, R$^3$, m, n, l, X, A ring and B ring are the same as defined in Formula (1)

In one aspect of the present invention, the compound represented by Formula (1-1) is any one of the compounds represented by the following Formulas (4) to (■).

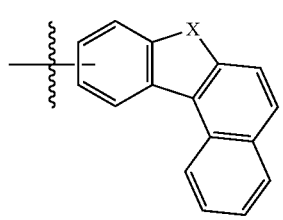

Formula (4)

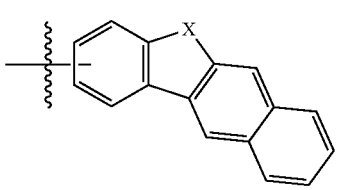

Formula (5)

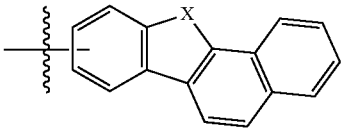

Formula (6)

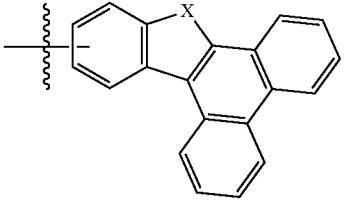

Formula (7)

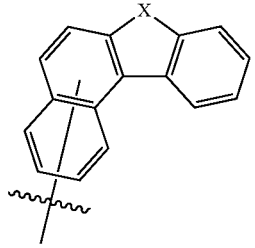

Formula (8)

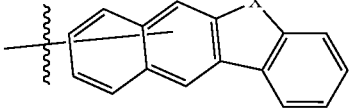

Formula (9)

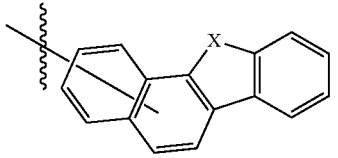

Formula (10)

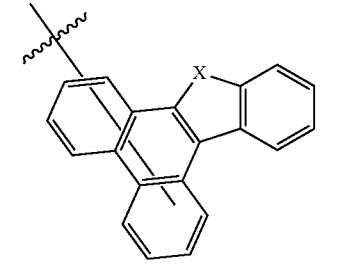

Formula (11)

(In Formula (4) to Formula (11), X is the same as defined in Formula (1).)

In a more specific aspect of the present invention, the compound represented by Formula (1) includes a compound represented by the following formulas.

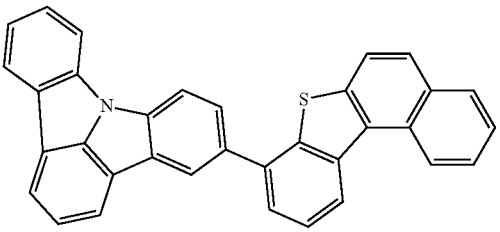

1-1

1-2
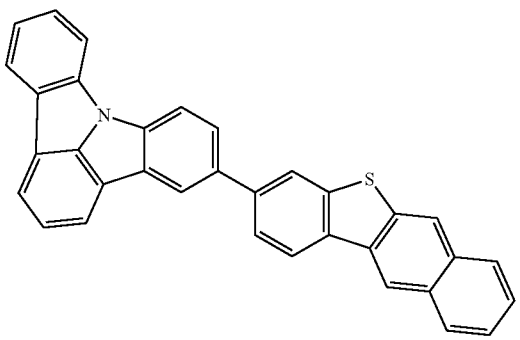
1-3
1-4
1-5
1-6
1-7
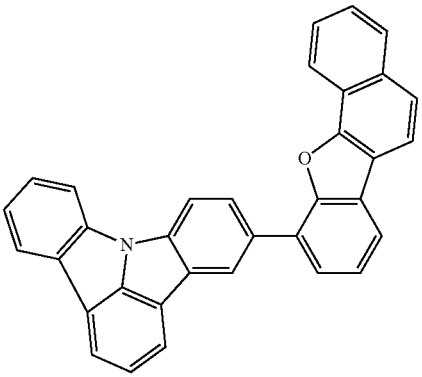
1-8
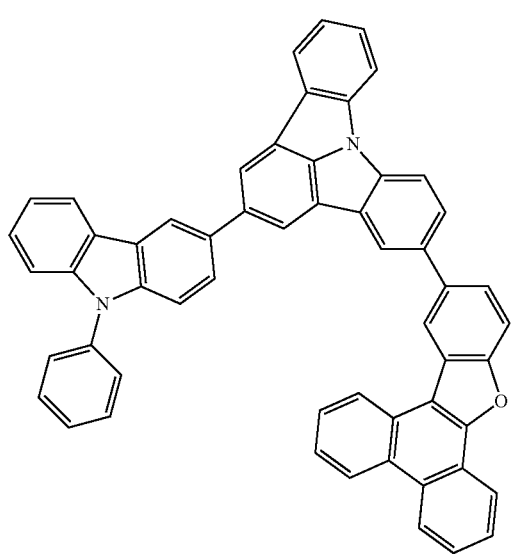
1-9
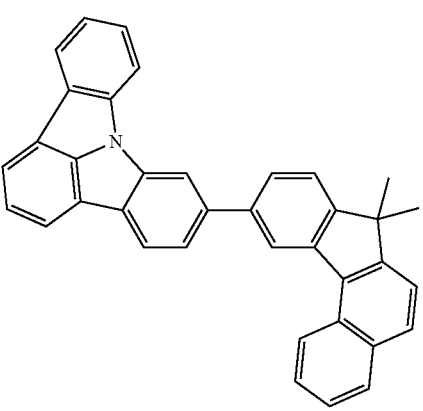

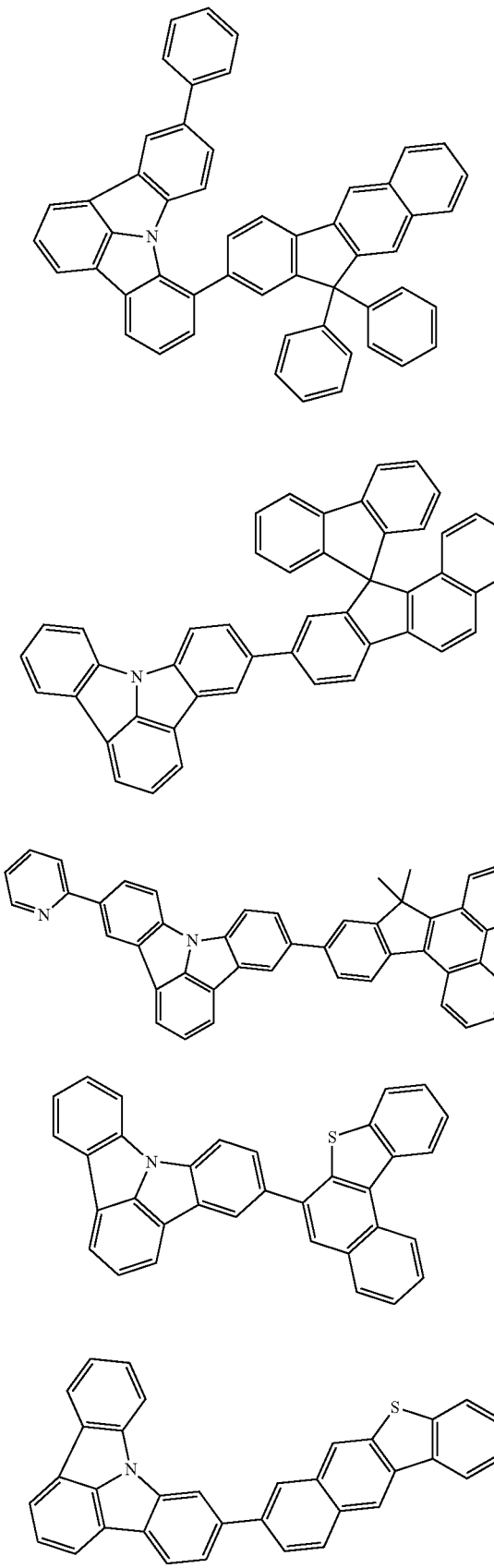
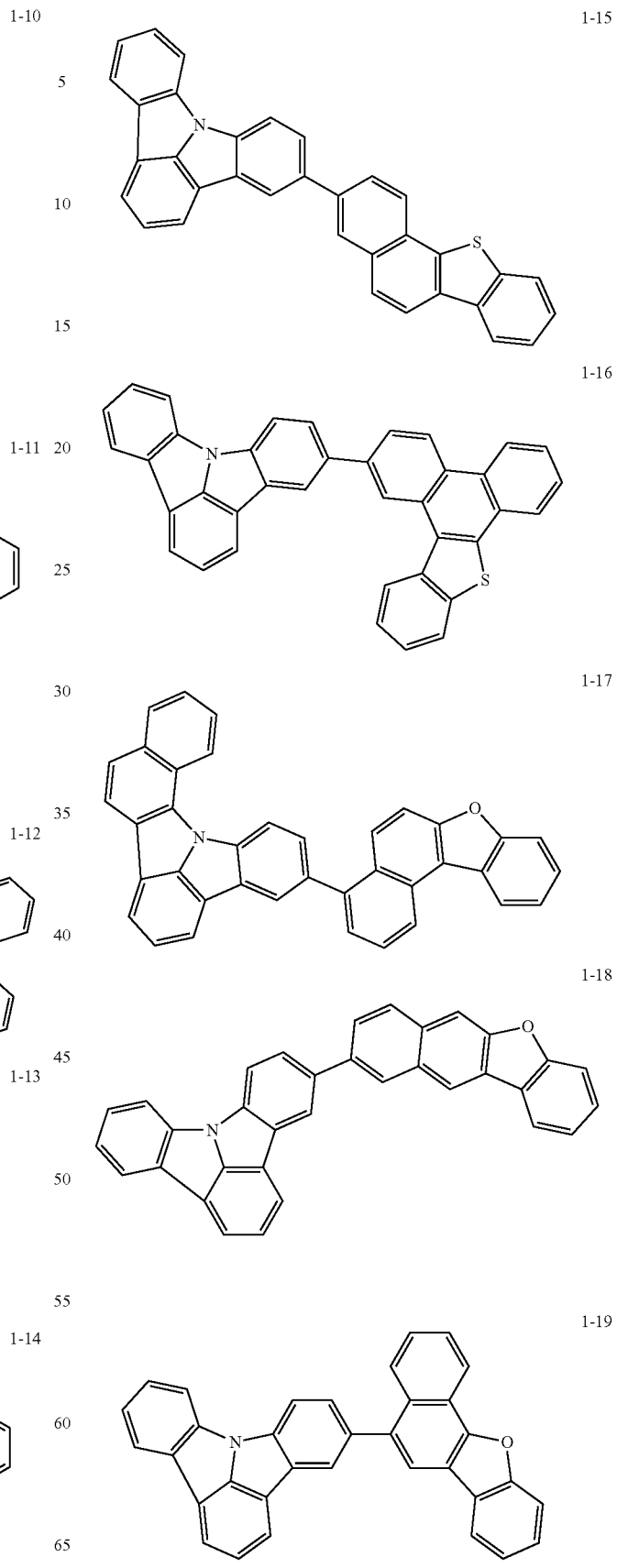

-continued
1-20
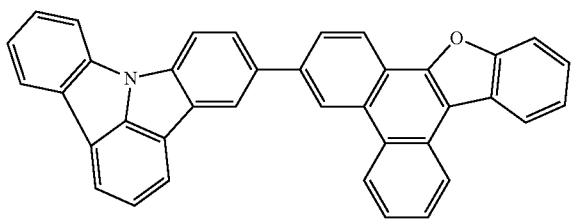
1-21
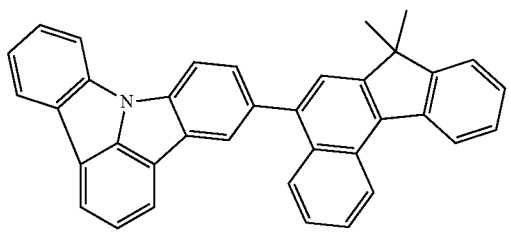
1-22
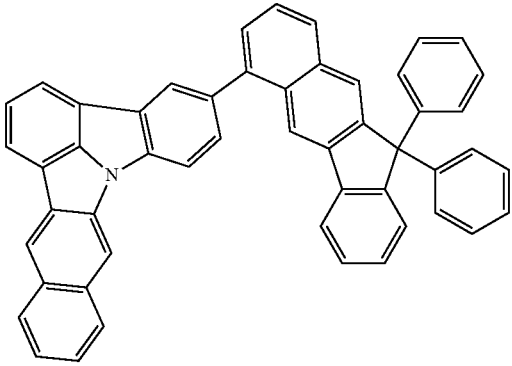
1-23
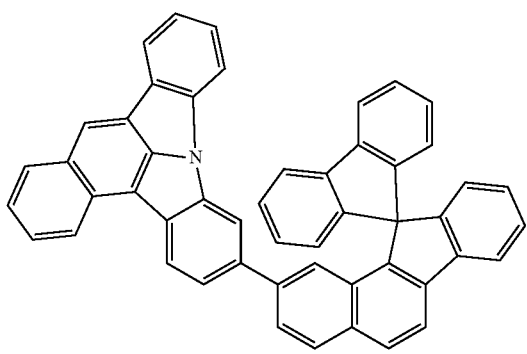
1-24
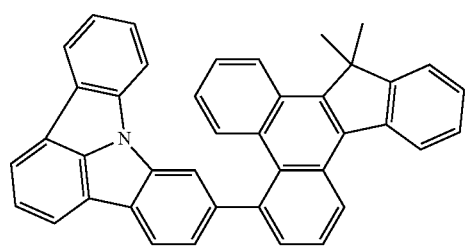
-continued
2-1
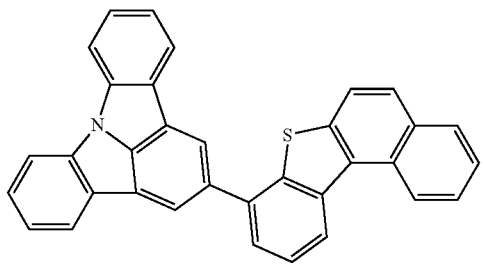
2-2
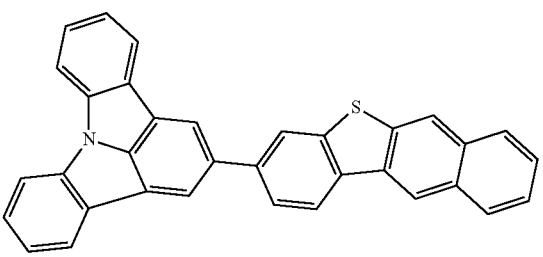
2-3
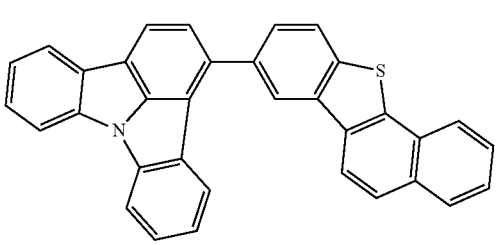
2-4
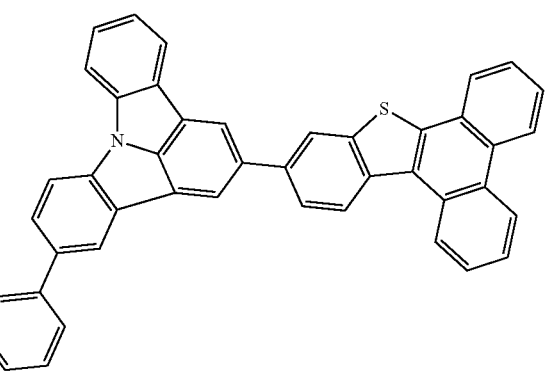
2-5
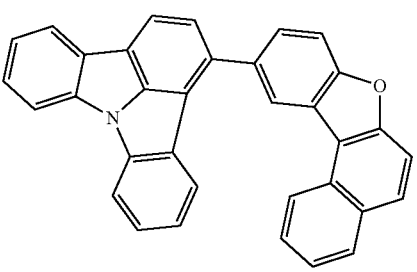

-continued
2-6
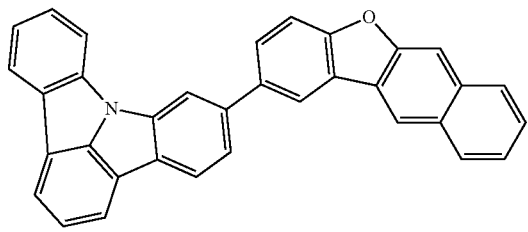
2-7
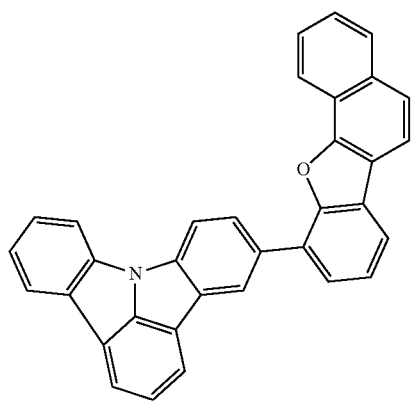
2-8
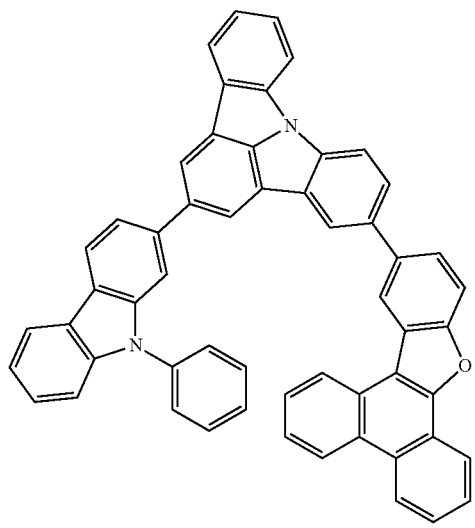
2-9
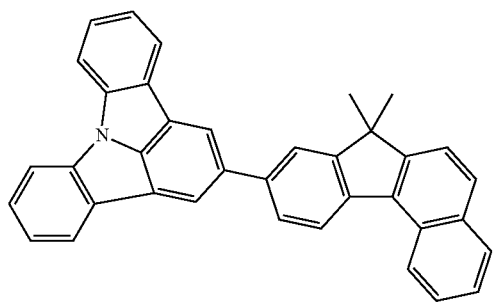
-continued
2-10
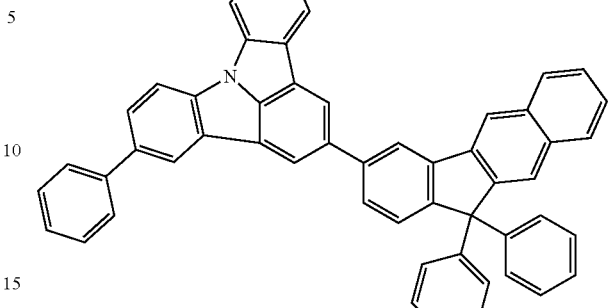
2-11
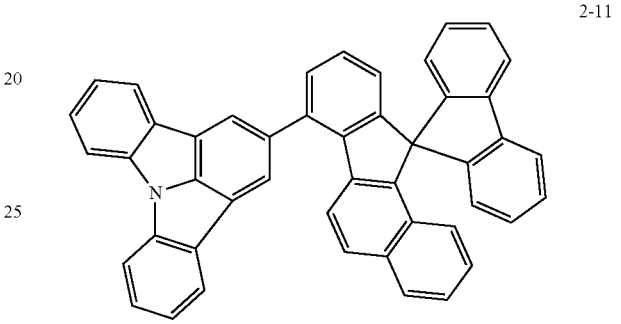
2-12
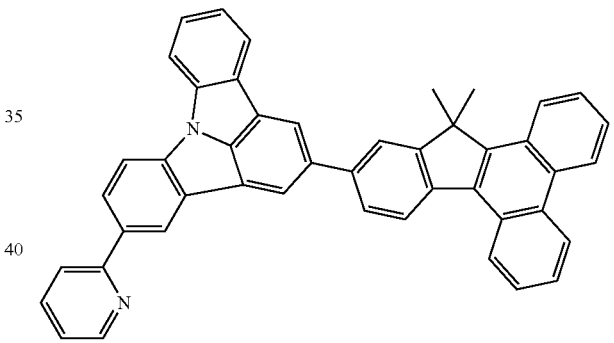
2-13
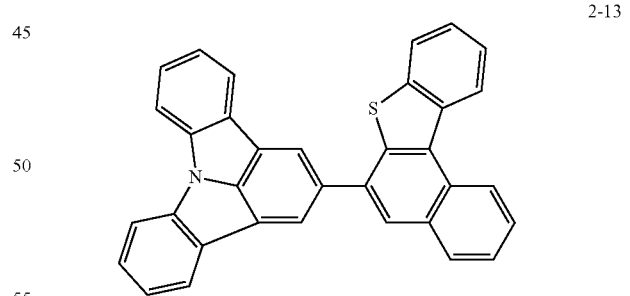
2-14
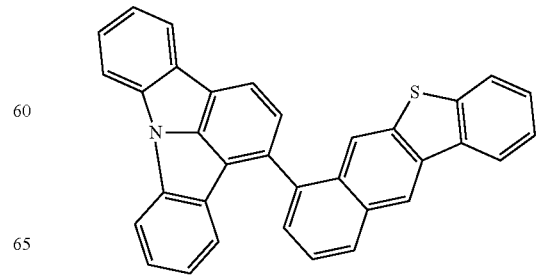

-continued
2-15
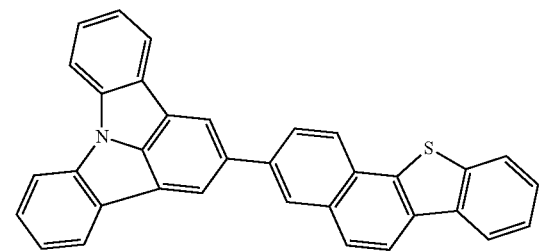
2-16
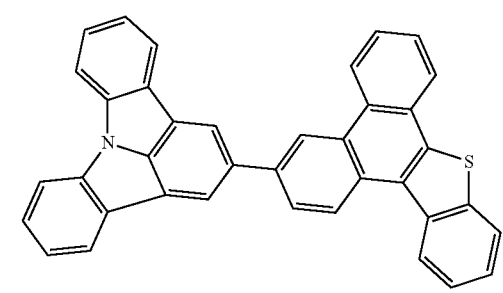
2-17
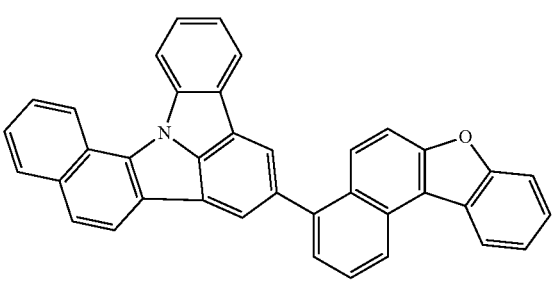
2-18
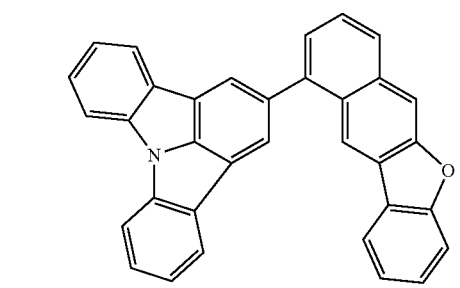
2-19
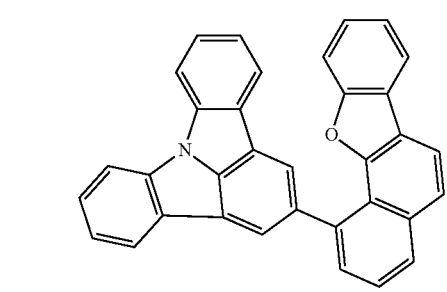
-continued
2-20
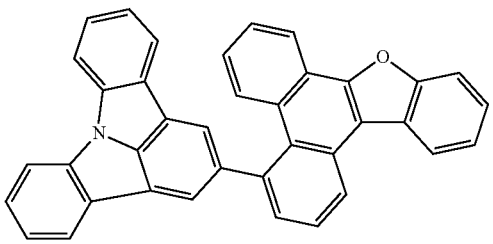
2-21
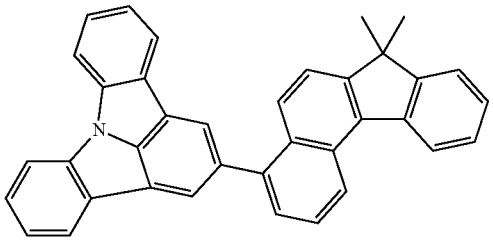
2-22
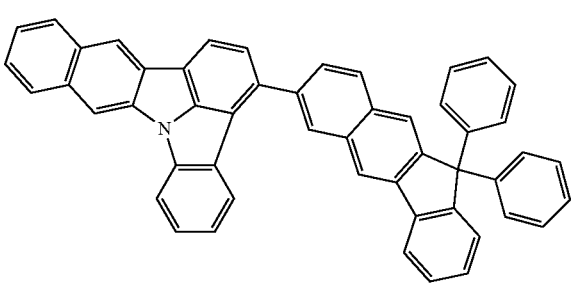
2-23
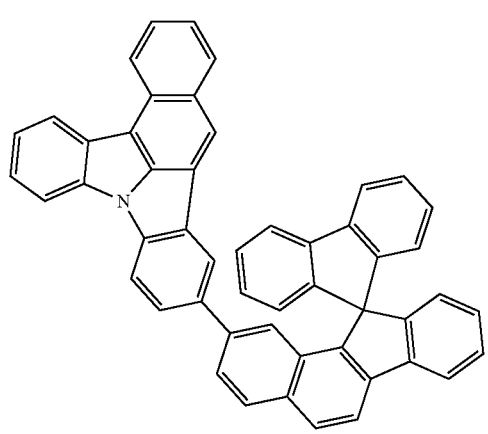
2-24
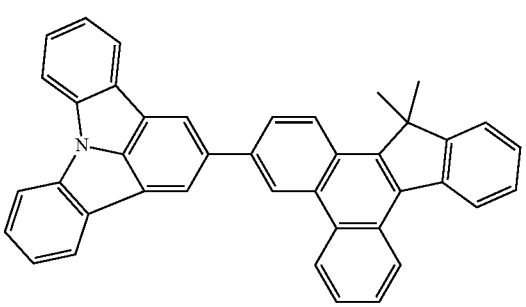
In another embodiment, the present invention provides a compound for an organic electric element represented by Formula (1).

In another embodiment, the present invention provides an organic electric element containing the compound represented by Formula (1).

The organic electric element includes a first electrode; a second electrode; and an organic material layer disposed between the first electrode and the second electrode; and the organic material layer may include a compound represented by Formula (1). In addition, the present invention may further include a light efficiency enhancing layer formed on at least one of the opposite side to the organic material layer, or one of the opposite side to the organic material layer among one side of the second electrode.

Also, in the present invention, the organic material layer is formed by one of a spin coating process, a nozzle printing process, an inkjet printing process, a slot coating process, a dip coating process or a roll-to-roll process, and The present invention also provides an organic electric element wherein the organic material layer comprises the compound as a phosphorescent host material of an emitting layer.

The present invention also provides an electronic device including a display device including the organic electric element; and a control part driving the display apparatus.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant(PDA), an electronic dictionary, a point-to-multipoint(PMP), a remote controller, a navigation unit, a game player, various kinds of TVs, and various kinds of computers.

Hereinafter, synthesis examples of the compound represented by Formula according to the present invention and preparation examples of the organic electric element will be described in detail by way of example, but are not limited to the following examples of the invention.

[Synthesis]

The final product represented by Formula (1) according to the present invention can be synthesized by reaction between Sub 1 and Sub 2 as illustrated in the following Reaction Scheme 1.

<Reaction Scheme 1>

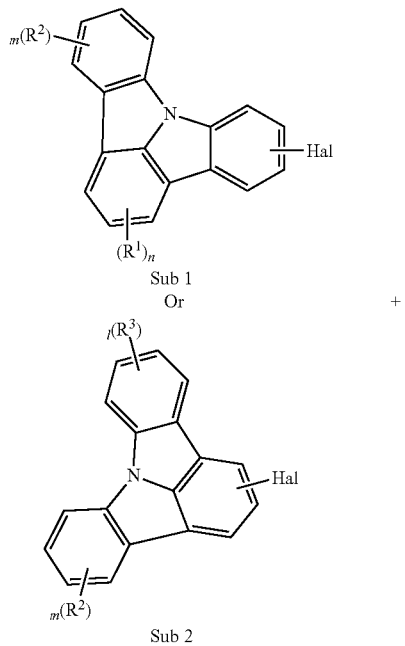

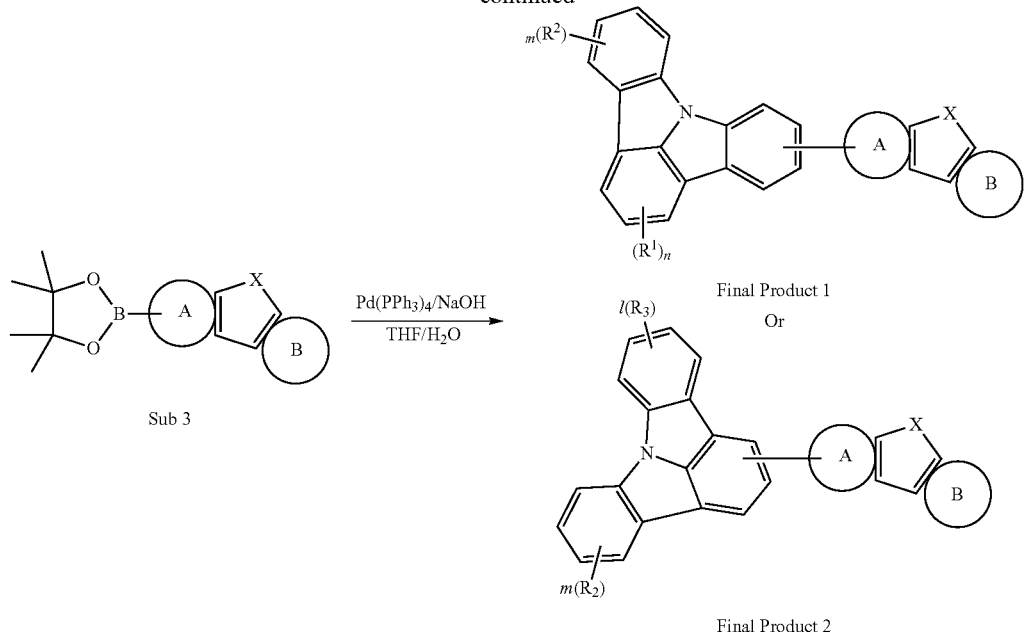

Final Product 1
Or

Final Product 2

SYNTHESIS EXAMPLES of 1-1

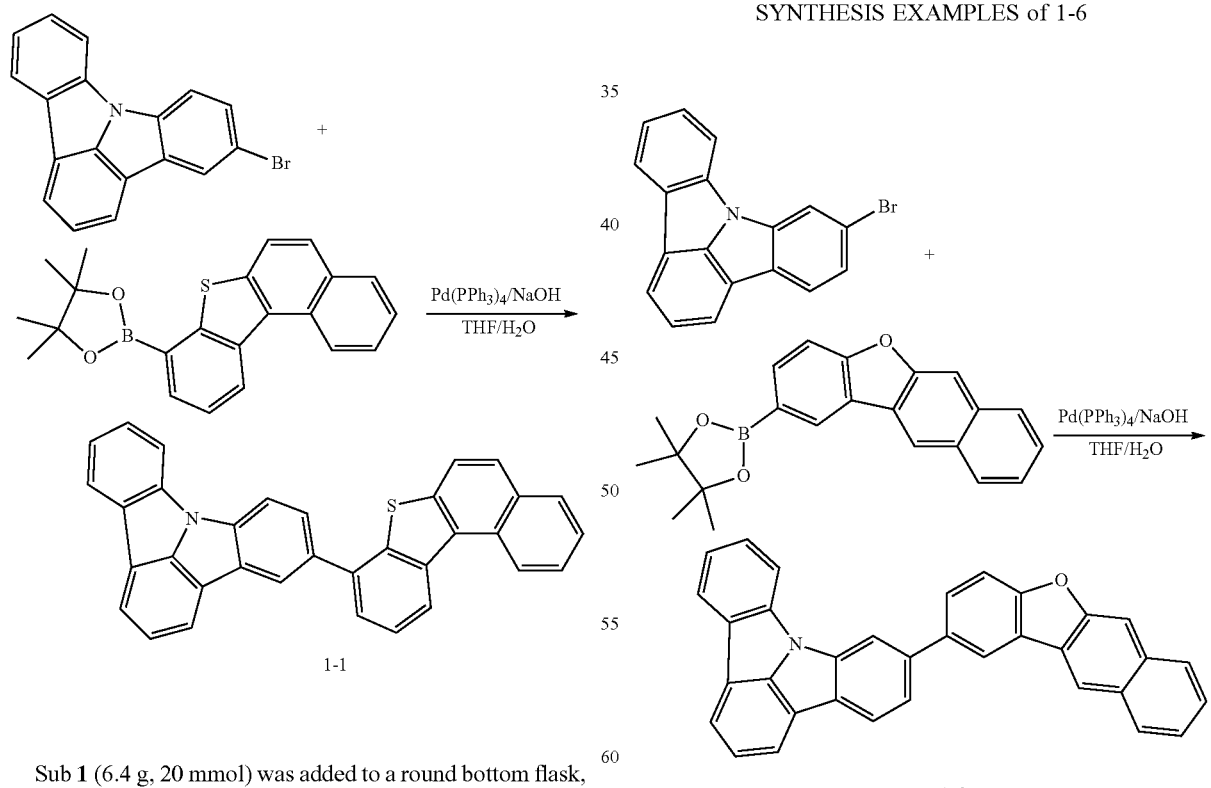

Sub 1 (6.4 g, 20 mmol) was added to a round bottom flask, and Sub 3 (7.2 g, 20 mmol), Pd(PPh$_3$)$_4$ (0.7 g, 0.6 mmol), NaOH (2.4 g, 60 mmol), THF (60 mL), 30 mL of water were added. Then, the mixture is heated to reflux at 80° C. to 90° C. When the reaction is complete, dilute with distilled water at room temperature and extract with methylene chloride and water. The organic layer was dried over MgSO4 and concentrated. The resulting compound was purified by silicagel column and recrystallized to obtain 7.5 g of the product. (Yield: 79%).

SYNTHESIS EXAMPLES of 1-6

A Sub 1 (6.4 g, 20 mmol) was added to a round bottom flask, and a Sub 3 (6.9 g, 20 mmol) was added, and 6.9 g of the product was obtained by the synthesis method of 1-1 above. (Yield: 75%).

SYNTHESIS EXAMPLES of 1-10
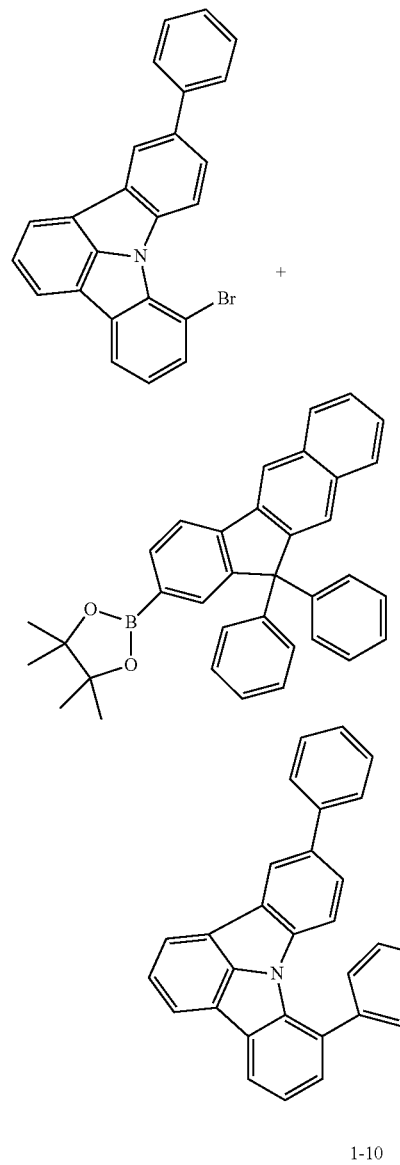
1-10
A Sub 1 (7.9 g, 20 mmol) was added to a round bottom flask, and a Sub 3 (9.9 g, 20 mmol) was added, and 10.1 g of the product was obtained by the synthesis method of 1-1 above. (Yield: 74%).
SYNTHESIS EXAMPLES of 1-11
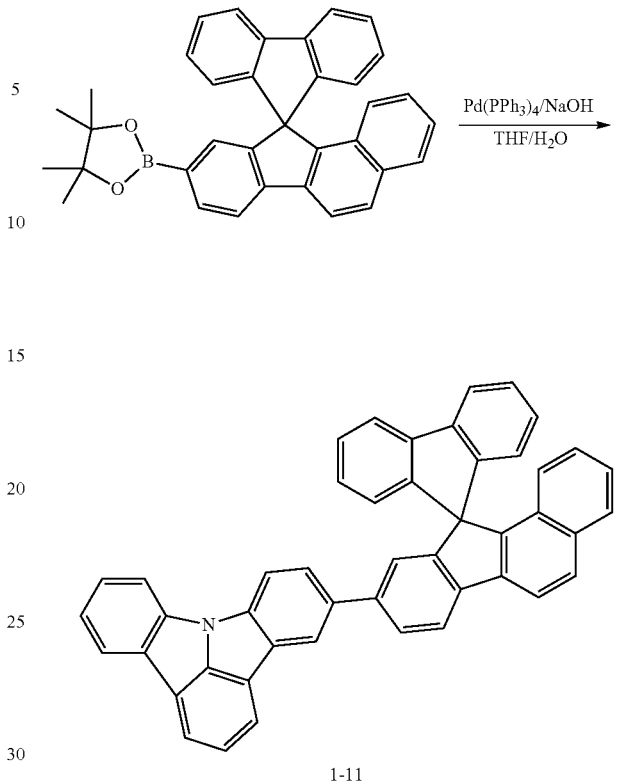
1-11
A Sub 1 (6.4 g, 20 mmol) was added to a round bottom flask, and a Sub 3 (9.8 g, 20 mmol) was added, and 9.4 g of the product was obtained by the synthesis method of 1-1 above. (Yield: 78%).
SYNTHESIS EXAMPLES of 1-15
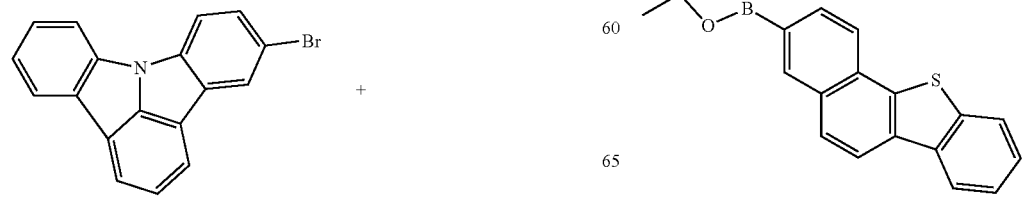

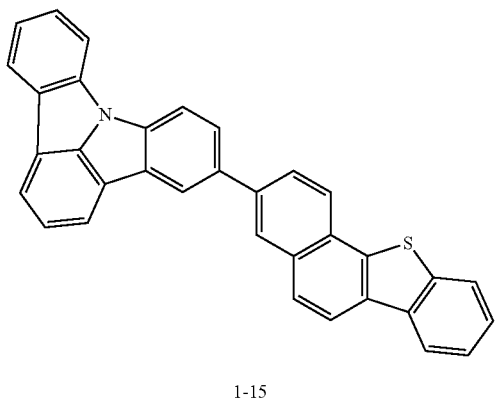

1-15

A Sub 1 (6.4 g, 20 mmol) was added to a round bottom flask, and a Sub 3 (7.2 g, 20 mmol) was added, and 7.1 g of the product was obtained by the synthesis method of 1-1 above. (Yield: 75%).

SYNTHESIS EXAMPLES of 1-17

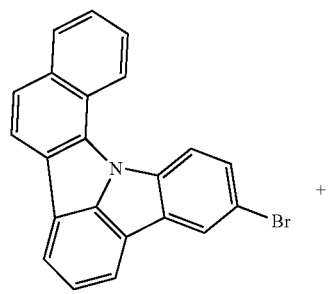

+

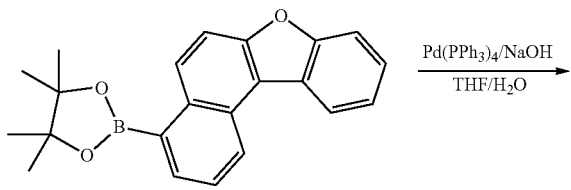

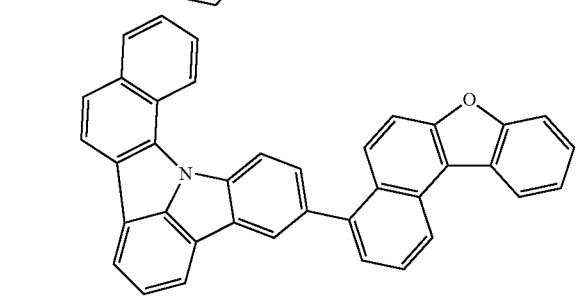

1-17

A Sub 1 (7.4 g, 20 mmol) was added to a round bottom flask, and a Sub 3 (6.9 g, 20 mmol) was added, and 7.3 g of the product was obtained by the synthesis method of 1-1 above. (Yield: 72%).

SYNTHESIS EXAMPLES of 1-21

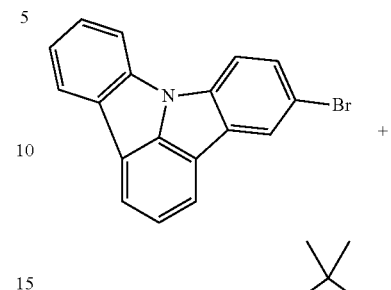

+

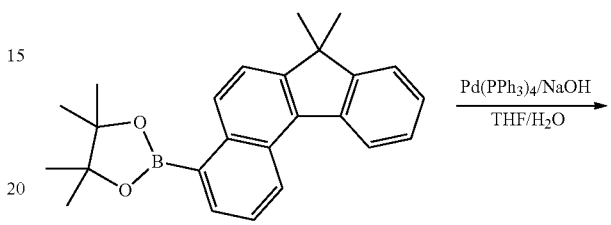

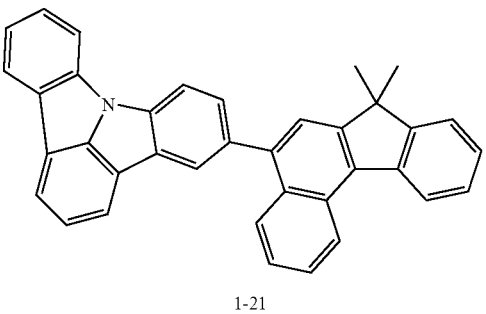

1-21

A Sub 1 (7.4 g, 20 mmol) was added to a round bottom flask, and a Sub 3 (7.4 g, 20 mmol) was added, and 7.5 g of the product was obtained by the synthesis method of 1-1 above. (Yield: 78%).

SYNTHESIS EXAMPLES of 2-3

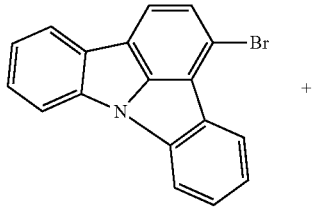

+

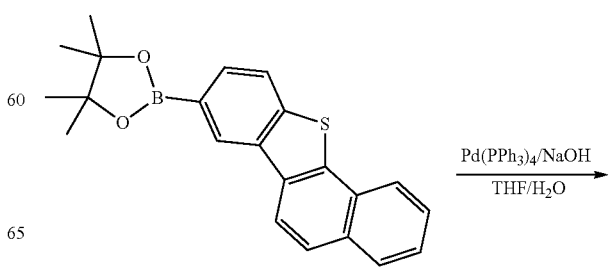

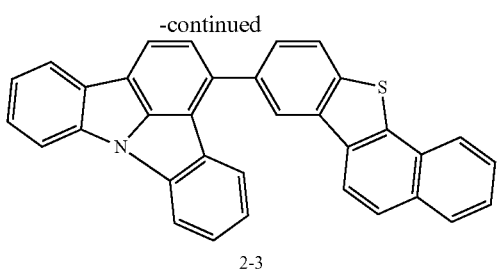

2-3

A Sub 2 (7.4 g, 20 mmol) was added to a round bottom flask, and a Sub 3 (7.2 g, 20 mmol) was added, and 6.9 g of the product was obtained by the synthesis method of 1-1 above. (Yield: 73%).

SYNTHESIS EXAMPLES of 2-8

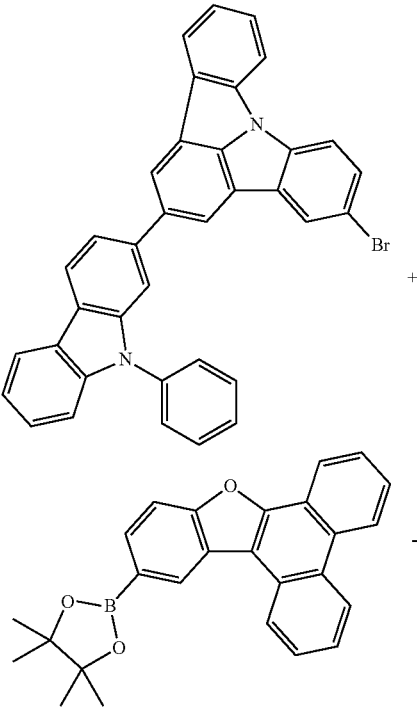

2-8

A Sub 2 (11.2 g, 20 mmol) was added to a round bottom flask, and a Sub 3 (7.9 g, 20 mmol) was added, and 10.6 g of the product was obtained by the synthesis method of 1-1 above. (Yield: 71%).

SYNTHESIS EXAMPLES of 2-12

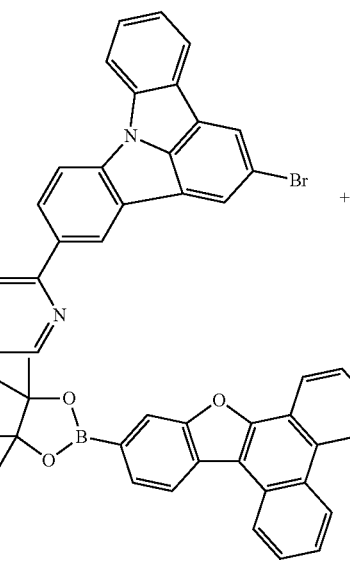

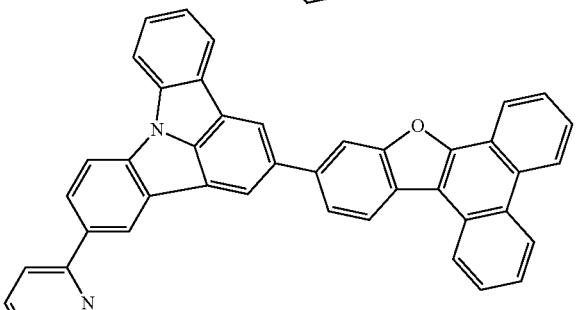

2-12

A Sub 2 (7.9 g, 20 mmol) was added to a round bottom flask, and a Sub 3 (8.4 g, 20 mmol) was added, and 9.3 g of the product was obtained by the synthesis method of 1-1 above. (Yield: 76%).

SYNTHESIS EXAMPLES of 2-14

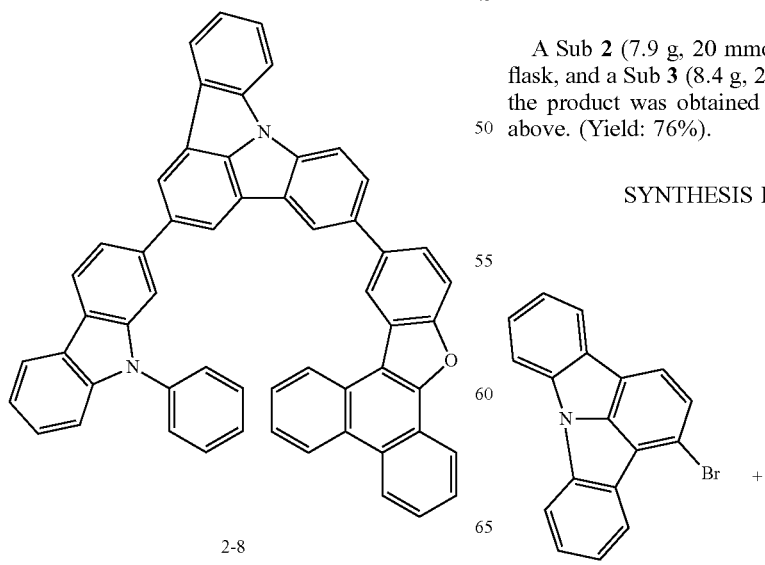

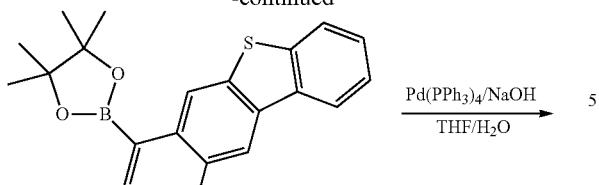

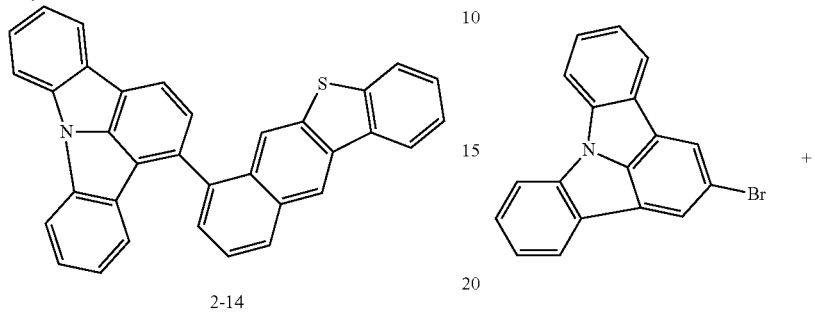

A Sub 2 (6.4 g, 20 mmol) was added to a round bottom flask, and a Sub 3 (7.2 g, 20 mmol) was added, and 7.4 g of the product was obtained by the synthesis method of 1-1 above. (Yield: 73%).

SYNTHESIS EXAMPLES of 2-21

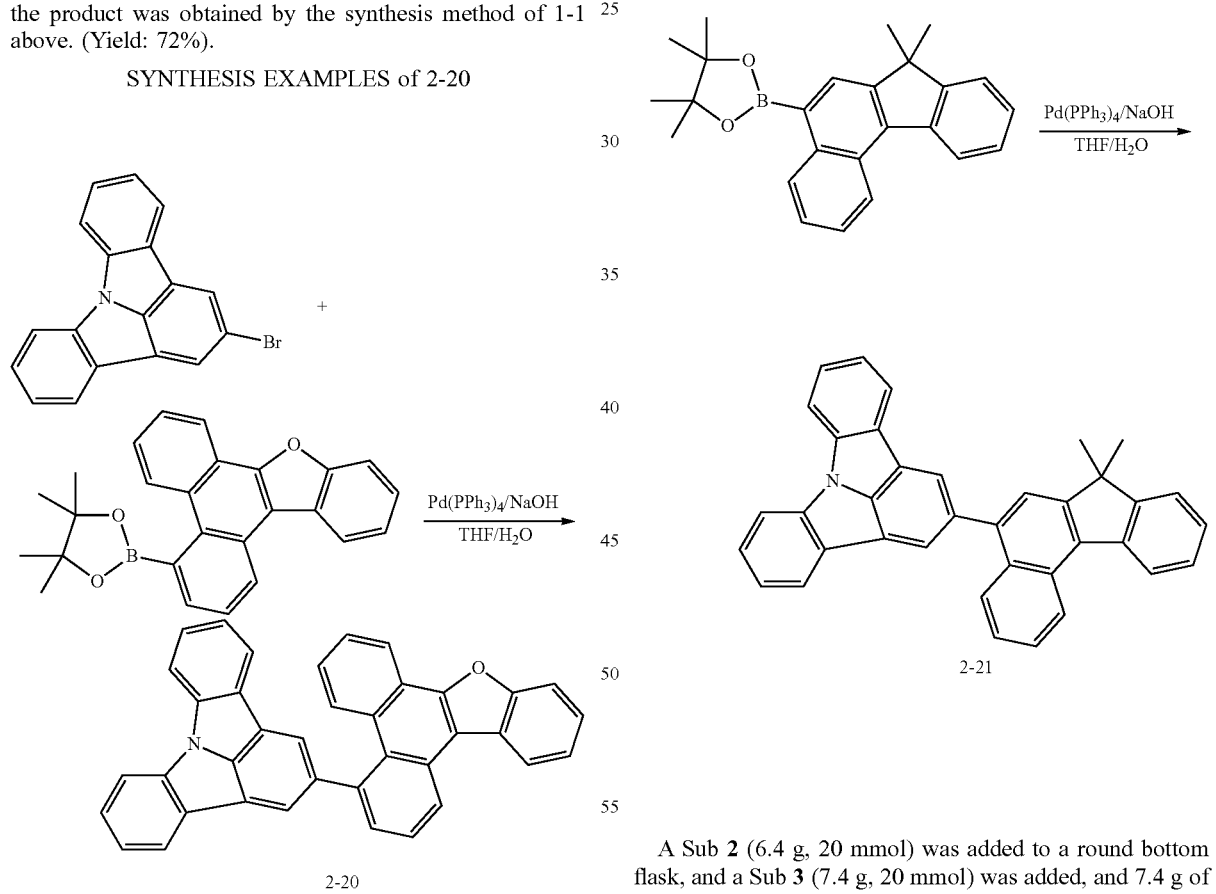

A Sub 2 (6.4 g, 20 mmol) was added to a round bottom flask, and a Sub 3 (7.2 g, 20 mmol) was added, and 6.8 g of the product was obtained by the synthesis method of 1-1 above. (Yield: 72%).

SYNTHESIS EXAMPLES of 2-20

A Sub 2 (6.4 g, 20 mmol) was added to a round bottom flask, and a Sub 3 (7.4 g, 20 mmol) was added, and 7.4 g of the product was obtained by the synthesis method of 1-1 above. (Yield: 76%).

TABLE 1

| compound | FD-MS | compound | FD-MS |
| --- | --- | --- | --- |
| 1-1 | m/z = 473.12($C_{34}H_{19}NS$ = 473.59) | 1-2 | m/z = 473.12($C_{34}H_{19}NS$ = 473.59) |
| 1-3 | m/z = 473.12($C_{34}H_{19}NS$ = 473.59) | 1-4 | m/z = 599.17($C_{44}H_{25}NS$ = 599.74) |

TABLE 1-continued

| compound | FD-MS | compound | FD-MS |
| --- | --- | --- | --- |
| 1-5 | m/z = 457.15($C_{34}H_{19}NO$ = 457.52) | 1-6 | m/z = 457.15($C_{34}H_{19}NO$ = 457.52) |
| 1-7 | m/z = 457.15($C_{34}H_{19}NO$ = 457.52) | 1-8 | m/z = 748.25($C_{56}H_{32}N_2O$ = 748.87) |
| 1-9 | m/z = 483.20($C_{37}H_{25}N$ = 483.60) | 1-10 | m/z = 683.26($C_{53}H_{33}N$ = 683.84) |
| 1-11 | m/z = 605.21($C_{47}H_{27}N$ = 605.72) | 1-12 | m/z = 610.24($C_{46}H_{30}N_2$ = 610.74) |
| 1-13 | m/z = 473.12($C_{34}H_{19}NS$ = 473.59) | 1-14 | m/z = 473.12($C_{34}H_{19}NS$ = 473.59) |
| 1-15 | m/z = 473.12($C_{34}H_{19}NS$ = 473.59) | 1-16 | m/z = 523.14($C_{38}H_{21}NS$ = 523.65) |
| 1-17 | m/z = 457.15($C_{34}H_{19}NO$ = 457.52) | 1-18 | m/z = 457.15($C_{34}H_{19}NO$ = 457.52) |
| 1-19 | m/z = 457.15($C_{34}H_{19}NO$ = 457.52) | 1-20 | m/z = 507.16($C_{38}H_{21}NO$ = 507.58) |
| 1-21 | m/z = 483.20($C_{37}H_{25}N$ = 483.60) | 1-22 | m/z = 657.25($C_{51}H_{31}N$ = 657.80) |
| 1-23 | m/z = 655.23($C_{51}H_{29}N$ = 655.78) | 1-24 | m/z = 533.21($C_{41}H_{27}N$ = 533.66) |
| 2-1 | m/z = 473.12($C_{34}H_{19}NS$ = 473.59) | 2-2 | m/z = 473.12($C_{34}H_{19}NS$ = 473.59) |
| 2-3 | m/z = 473.12($C_{34}H_{19}NS$ = 473.59) | 2-4 | m/z = 599.17($C_{44}H_{25}NS$ = 599.74) |
| 2-5 | m/z = 457.15($C_{34}H_{19}NO$ = 457.52) | 2-6 | m/z = 457.15($C_{34}H_{19}NO$ = 457.52) |
| 2-7 | m/z = 457.15($C_{34}H_{19}NO$ = 457.52) | 2-8 | m/z = 748.25($C_{56}H_{32}N_2O$ = 748.87) |
| 2-9 | m/z = 483.20($C_{37}H_{25}N$ = 483.60) | 2-10 | m/z = 683.26($C_{53}H_{33}N$ = 683.84) |
| 2-11 | m/z = 605.21($C_{47}H_{27}N$ = 605.72) | 2-12 | m/z = 610.24($C_{46}H_{30}N_2$ = 610.74) |
| 2-13 | m/z = 473.12($C_{34}H_{19}NS$ = 473.59) | 2-14 | m/z = 473.12($C_{34}H_{19}NS$ = 473.59) |
| 2-15 | m/z = 473.12($C_{34}H_{19}NS$ = 473.59) | 2-16 | m/z = 523.14($C_{38}H_{21}NS$ = 523.65) |
| 2-17 | m/z = 457.15($C_{34}H_{19}NO$ = 457.52) | 2-18 | m/z = 457.15($C_{34}H_{19}NO$ = 457.52) |
| 2-19 | m/z = 457.15($C_{34}H_{19}NO$ = 457.52) | 2-20 | m/z = 507.16($C_{38}H_{21}NO$ = 507.58) |
| 2-21 | m/z = 483.20($C_{37}H_{25}N$ = 483.60) | 2-22 | m/z = 657.25($C_{51}H_{31}N$ = 657.80) |
| 2-23 | m/z = 655.23($C_{51}H_{29}N$ = 655.78) | 2-24 | m/z = 533.21($C_{41}H_{27}N$ = 533.66) |

Manufacture and Evaluation of Organic Electric Element

Example 1

Manufacture and Evaluation of Green Organic Light Emitting Device (Phosphorescent Host)

An organic electroluminescent device was fabricated according to a conventional method using a compound obtained through synthesis as a host material of an emitting layer. First, on an ITO layer(anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm, and subsequently, on this film, 4,4-bis [N-(1-naphthyl)-N-phenylamino]biphenyl (hereinafter will be abbreviated as NPB) as a hole transporting compound was vacuum-deposited to form a hole transport layer with a thickness of 60 nm. On the hole transport layer, the inventive compound or comparative compound A [CBP(4,4'-N,N-dicarbazole-biphenyl)] or comparative compound B or comparative compound C were used as a host, and as a dopant, an emitting layer with a thickness of 30 nm was deposited on the hole transport layer by doping Ir(ppy)₃ [tris(2-phenylpyridine)-iridium] with a weight of 95:5. (1,1'-biphenyl)-4-olato)bis(2-methyl-8-quinolinolato)aluminum (hereinafter abbreviated as BAlq) was vacuum deposited as a hole blocking layer to a thickness of 10 nm, and tris(8-quinolinol) aluminum (hereinafter abbreviated as Alq3) was deposited to a thickness of 40 nm as an electron injection layer. After that, an alkali metal halide, LiF was vacuum deposited to a thickness of 0.2 nm, and subsequently, Al was deposited to a thickness of 150 nm and the Al/LiF was used as a cathode to produce an organic electroluminescent device.

To the OLEDs which were manufactured by examples and comparative examples, a forward bias direct current voltage was applied, and electroluminescent(EL) properties were measured using PR-650 of Photoresearch Co., and T95 life was measured using a life measuring apparatus manufactured by McScience Inc. with a reference luminance of 500 cd/m². In the following table, the manufacture of a device and the results of evaluation are shown.

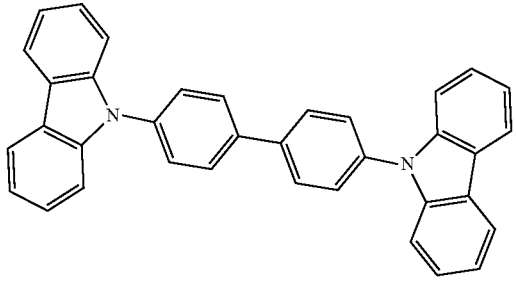

Comparative compound A

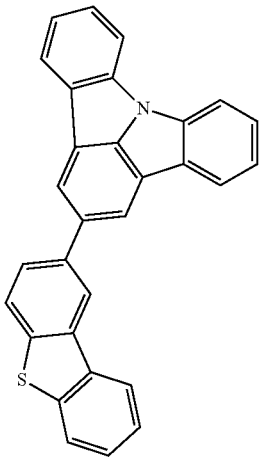

Comparative compound B

Comparative compound C

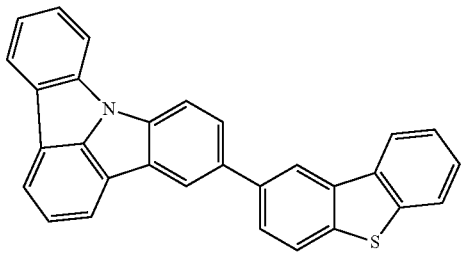

TABLE 2

| | compound | Voltage | Current Density | Brightness (cd/m2) | Efficiency | Lifetime T(95) | CIE (x, y) |
|---|---|---|---|---|---|---|---|
| comparative example(1) | compound (A) | 5.9 | 21.2 | 5000.0 | 23.6 | 56.1 | (0.31, 0.60) |
| comparative example (2) | compound (B) | 5.5 | 14.5 | 5000.0 | 34.5 | 93.7 | (0.31, 0.61) |
| comparative example(3) | compound (C) | 5.6 | 14.8 | 5000.0 | 33.8 | 95.5 | (0.31, 0.60) |
| example(1) | compound(1-1) | 5.2 | 11.4 | 5000.0 | 44.0 | 114.9 | (0.30, 0.60) |
| example(2) | compound(1-2) | 5.3 | 11.4 | 5000.0 | 43.8 | 117.3 | (0.31, 0.61) |
| example(3) | compound(1-3) | 5.2 | 11.5 | 5000.0 | 43.7 | 113.2 | (0.31, 0.60) |
| example(4) | compound(1-4) | 5.1 | 11.4 | 5000.0 | 44.0 | 112.5 | (0.33, 0.61) |
| example(5) | compound(1-5) | 5.2 | 12.1 | 5000.0 | 41.3 | 111.9 | (0.32, 0.61) |
| example(6) | compound(1-6) | 5.3 | 12.0 | 5000.0 | 41.8 | 116.8 | (0.33, 0.60) |
| example(7) | compound(1-7) | 5.1 | 12.0 | 5000.0 | 41.5 | 115.8 | (0.32, 0.61) |
| example(8) | compound(1-8) | 5.3 | 12.2 | 5000.0 | 41.1 | 115.2 | (0.31, 0.60) |
| example(9) | compound(1-9) | 5.3 | 12.7 | 5000.0 | 39.2 | 119.0 | (0.31, 0.61) |
| example(10) | compound(1-10) | 5.2 | 12.6 | 5000.0 | 39.8 | 115.0 | (0.31, 0.60) |
| example(11) | compound(1-11) | 5.2 | 12.7 | 5000.0 | 39.4 | 111.1 | (0.33, 0.61) |
| example(12) | compound(1-12) | 5.2 | 13.0 | 5000.0 | 38.5 | 116.1 | (0.30, 0.60) |
| example(13) | compound(1-13) | 5.2 | 11.6 | 5000.0 | 43.0 | 117.9 | (0.31, 0.61) |
| example(14) | compound(1-14) | 5.1 | 11.5 | 5000.0 | 43.5 | 111.2 | (0.31, 0.60) |
| example(15) | compound(1-15) | 5.3 | 11.4 | 5000.0 | 44.0 | 118.6 | (0.33, 0.61) |
| example(16) | compound(1-16) | 5.1 | 11.5 | 5000.0 | 43.5 | 115.1 | (0.32, 0.61) |
| example(17) | compound(1-17) | 5.1 | 12.0 | 5000.0 | 41.6 | 114.2 | (0.33, 0.60) |
| example(18) | compound(1-18) | 5.1 | 12.2 | 5000.0 | 41.1 | 114.4 | (0.32, 0.61) |
| example(19) | compound(1-19) | 5.1 | 12.1 | 5000.0 | 41.4 | 146.2 | (0.31, 0.60) |
| example(20) | compound(1-20) | 5.2 | 12.0 | 5000.0 | 41.7 | 119.6 | (0.31, 0.61) |
| example(21) | compound(1-21) | 5.2 | 13.1 | 5000.0 | 38.2 | 117.3 | (0.31, 0.60) |
| example(22) | compound(1-22) | 5.2 | 12.7 | 5000.0 | 39.3 | 110.6 | (0.33, 0.61) |
| example(23) | compound(1-23) | 5.3 | 13.1 | 5000.0 | 38.3 | 116.7 | (0.30, 0.60) |

TABLE 2-continued

| | compound | Voltage | Current Density | Brightness (cd/m2) | Efficiency | Lifetime T(95) | CIE (x, y) |
|---|---|---|---|---|---|---|---|
| example(24) | compound(1-24) | 5.3 | 12.6 | 5000.0 | 39.6 | 110.6 | (0.31, 0.61) |
| example(25) | compound(2-1) | 5.1 | 10.9 | 5000.0 | 45.8 | 110.6 | (0.31, 0.61) |
| example(26) | compound(2-2) | 5.1 | 11.0 | 5000.0 | 45.4 | 114.9 | (0.31, 0.60) |
| example(27) | compound(2-3) | 5.0 | 11.0 | 5000.0 | 45.6 | 111.1 | (0.33, 0.61) |
| example(28) | compound(2-4) | 4.9 | 11.0 | 5000.0 | 45.3 | 113.0 | (0.32, 0.61) |
| example(29) | compound(2-5) | 5.1 | 11.6 | 5000.0 | 43.0 | 111.4 | (0.33, 0.60) |
| example(30) | compound(2-6) | 4.9 | 11.4 | 5000.0 | 44.0 | 118.7 | (0.32, 0.61) |
| example(31) | compound(2-7) | 5.1 | 11.4 | 5000.0 | 43.7 | 119.8 | (0.31, 0.60) |
| example(32) | compound(2-8) | 5.1 | 11.6 | 5000.0 | 43.1 | 113.0 | (0.31, 0.61) |
| example(33) | compound(2-9) | 5.0 | 12.0 | 5000.0 | 41.7 | 119.2 | (0.31, 0.60) |
| example(34) | compound(2-10) | 5.0 | 12.1 | 5000.0 | 41.2 | 111.1 | (0.33, 0.61) |
| example(35) | compound(2-11) | 5.1 | 11.9 | 5000.0 | 41.9 | 113.0 | (0.30, 0.60) |
| example(36) | compound(2-12) | 5.0 | 12.2 | 5000.0 | 41.0 | 112.5 | (0.31, 0.61) |
| example(37) | compound(2-13) | 4.9 | 10.9 | 5000.0 | 45.7 | 119.9 | (0.31, 0.60) |
| example(38) | compound(2-14) | 5.0 | 10.9 | 5000.0 | 45.8 | 110.8 | (0.33, 0.61) |
| example(39) | compound(2-15) | 4.9 | 11.0 | 5000.0 | 45.3 | 113.6 | (0.32, 0.61) |
| example(40) | compound(2-16) | 5.1 | 11.1 | 5000.0 | 45.1 | 112.0 | (0.33, 0.60) |
| example(41) | compound(2-17) | 5.1 | 11.4 | 5000.0 | 44.0 | 118.9 | (0.32, 0.61) |
| example(42) | compound(2-18) | 5.0 | 11.5 | 5000.0 | 43.5 | 118.2 | (0.31, 0.60) |
| example(43) | compound(2-19) | 4.9 | 11.5 | 5000.0 | 43.5 | 119.1 | (0.31, 0.61) |
| example(44) | compound(2-20) | 5.0 | 11.5 | 5000.0 | 43.3 | 110.3 | (0.31, 0.60) |
| example(45) | compound(2-21) | 5.0 | 12.0 | 5000.0 | 41.7 | 114.4 | (0.33, 0.61) |
| example(46) | compound(2-22) | 4.9 | 12.2 | 5000.0 | 41.1 | 112.2 | (0.30, 0.60) |
| example(47) | compound(2-23) | 5.0 | 12.0 | 5000.0 | 41.7 | 110.2 | (0.31, 0.61) |
| example(48) | compound(2-24) | 4.9 | 12.1 | 5000.0 | 41.4 | 114.7 | (0.31, 0.60) |

As can be seen from the results of Table 2, the organic electroluminescent device using the organic electroluminescent device material of the present invention as a phosphorescent host can remarkably improve the efficiency and the driving voltage.

That is, Comparative compound B and Comparative compound C in which the core is substituted with indolocarbazole with Dibenzothiophen exhibited lower driving voltage, higher efficiency and higher lifetime than the comparative compound A, which is CBP generally used as a host material, and the compounds of the present invention in which fused compounds were substituted in addition to Dibenzothiophen fused to the same core as the comparative compound B and comparative compound C showed the best device results as compared with the comparative compounds.

It is presumed that the inventive compound has better stability against Hole as well as electron than the comparative compounds B and C while having the fused compound as a substituent, thereby improving the lifetime of the device, and the charge balance in the emitting layer of the hole and the electron is increased, the light emission is well performed in the emitting layer, and when the device is fused, packing density is further improved during device deposition to maximize drive voltage, efficiency and lifetime.

That is, this suggests that even if the same core is used, the characteristics of the compound and the element may be significantly changed depending on the kind of the substituent (presence or absence of fused).

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula (1) below:

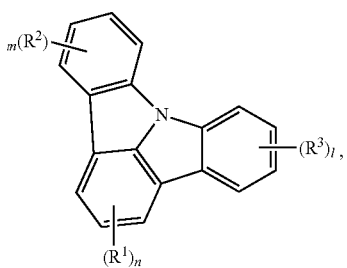

Formula (1)

wherein m and l are each an integer of 0 to 4,
n is an integer of 0 to 3,
at least one of $R^1$, $R^2$ and $R^3$ is represented by any of Formulas (4) to (11):

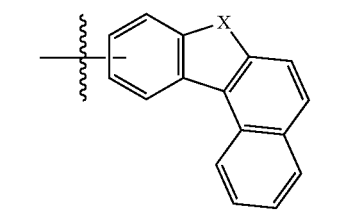

Formula (4)

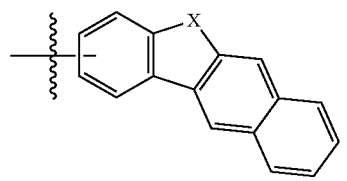

Formula (5)

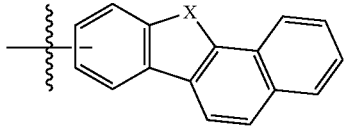

Formula (6)

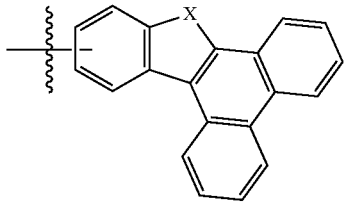

Formula (7)

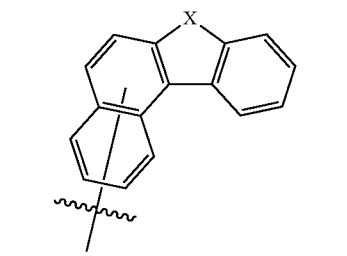

Formula (8)

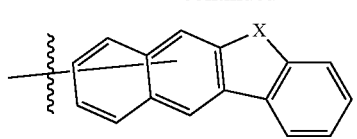

Formula (9)

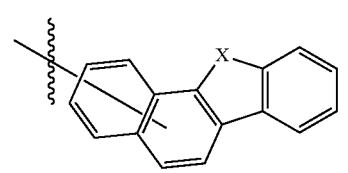

Formula (10)

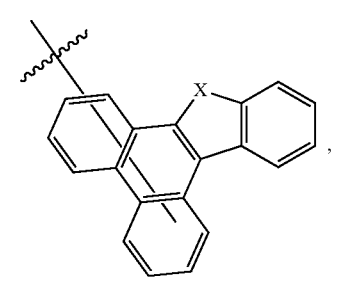

Formula (11)

and the remaining $R^1$, $R^2$ and/or $R^3$ not represented by any of Formulas (4) to (11) are each independently selected from the group consisting of deuterium; a halogen; a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L-N($R_a$)($R_b$), wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, and P, wherein when m, n, and l are an integer of 2 or more, $R^1$, $R^2$ and $R^3$ are each in plural being the same or different from each other, and a plurality of $R^1$s or a plurality of $R^2$s or a plurality of $R^3$s may combine to each other to form an aromatic or a heteroaromatic ring, and X is i) O or S in Formulas (4) to (11) and in this case the remaining $R^1$ to $R^3$ not represented by Formulas (4) to (11) are in plural, and a plurality of $R^1$s, $R^2$s, or $R^3$s combine to each other to form an aromatic or a heteroaromatic ring, or ii) O, S, or CR'R" in Formula (7) and (11), and CR'R" in Formulas (4) to (6) and (8) to (10), wherein R' and R" are each independently a $C_1$-$C_{50}$ alkyl group; a $C_6$-$C_{60}$ aryl group; a $C_2$-$C_{60}$ heterocyclic group including at least one hetero atom of O, N, S, Si and P; and may be bonded to each other to form a spiro, wherein the aryl group, heteroaryl group, fluorenyl group, arylene group, heterocyclic group, or fused ring group of $R^1$, $R^2$, $R^3$, R' and R" may be substituted with one or more substituents selected from the group consisting of deuterium; halogen; a silane group; siloxane group; boron group; germanium group; cyano group; nitro group;-L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, wherein the substituents may combine to each other to form a ring, saturated or unsaturated, selected from the group consisting of a $C_3$-$C_{60}$ aliphatic ring, a $C_6$-$C_{60}$ aromatic ring, a $C_2$-$C_{60}$ heterocyclic ring, and a fused ring formed by combination thereof.

2. A compound selected from the group consisting of the following formulas:

1-4
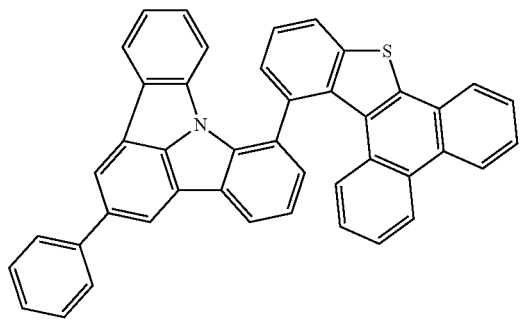

1-8
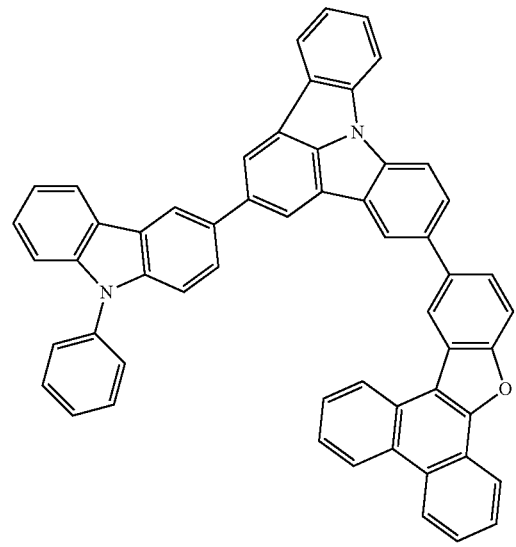

1-9
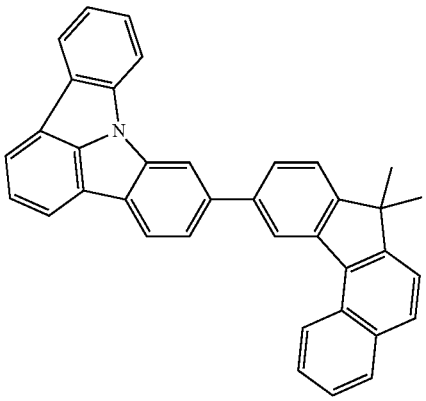

1-10
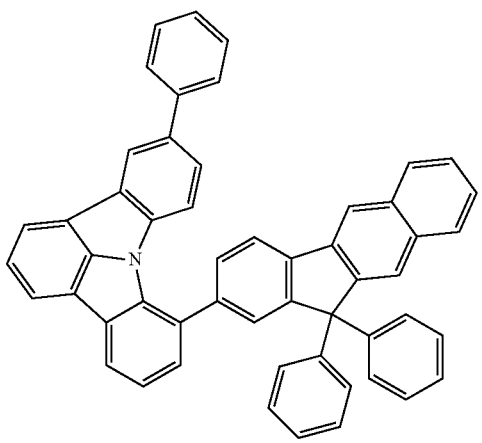

1-11, 1-12
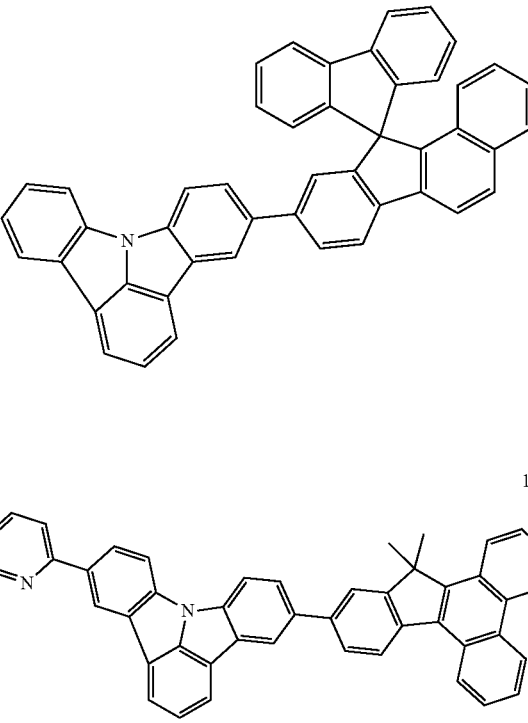

1-16
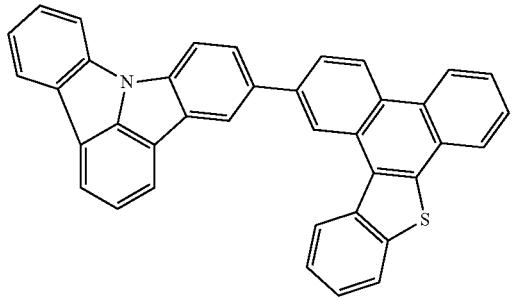
1-17
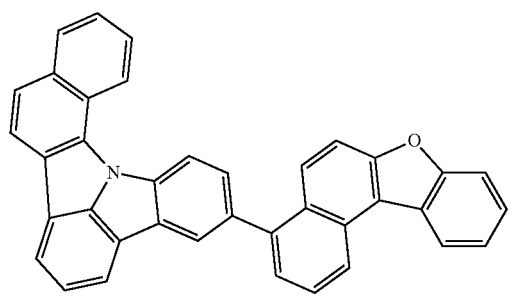
1-20
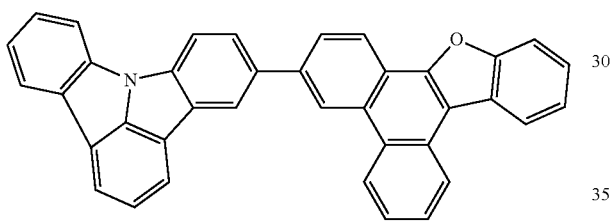
1-21
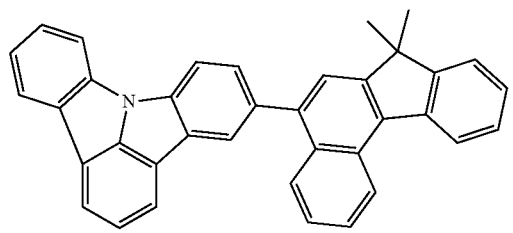
1-22
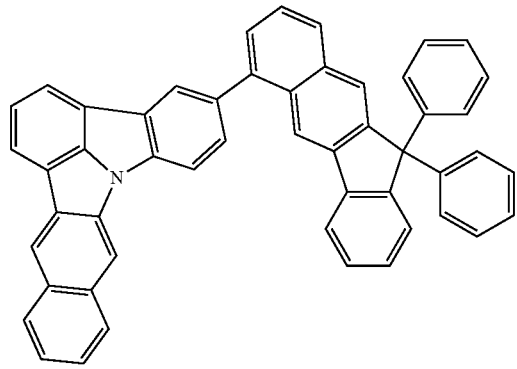
1-23
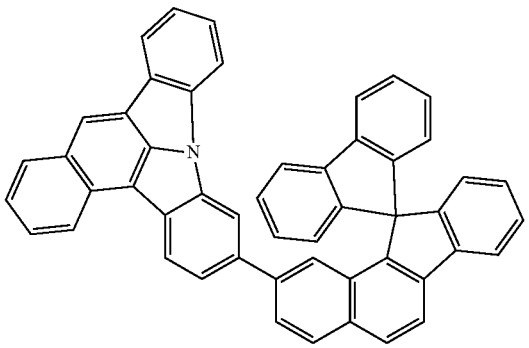
1-24
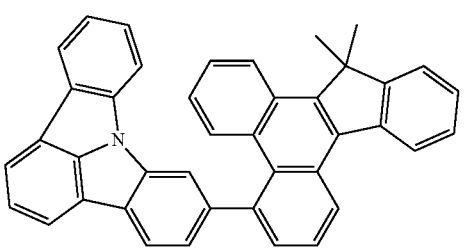
2-4
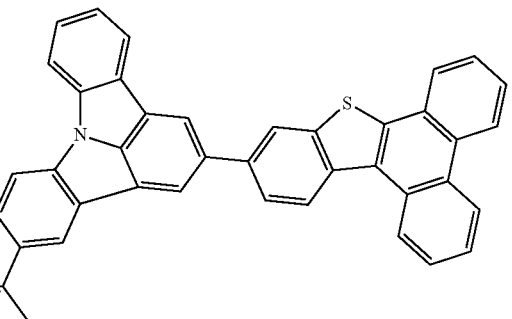
2-8
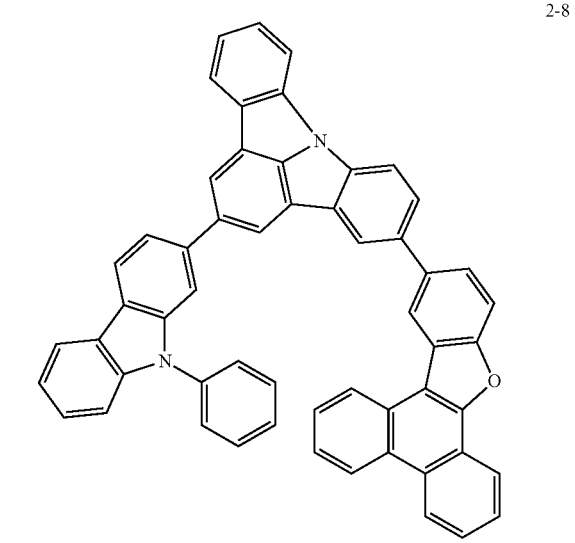

2-9
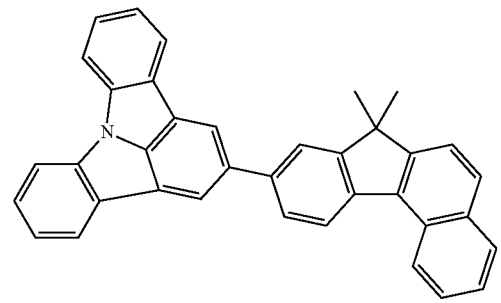
2-14
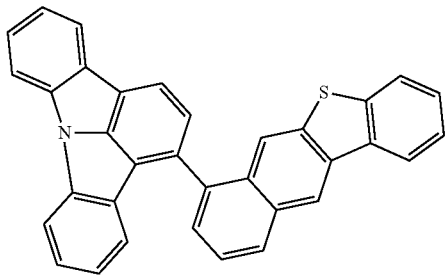
2-10
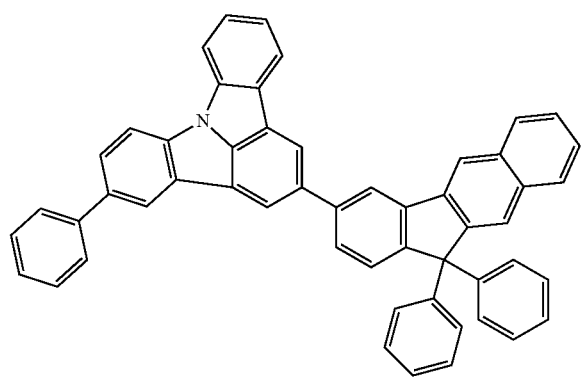
2-15
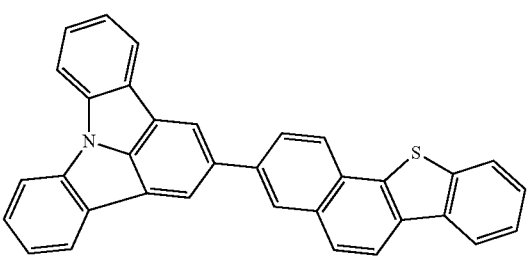
2-16
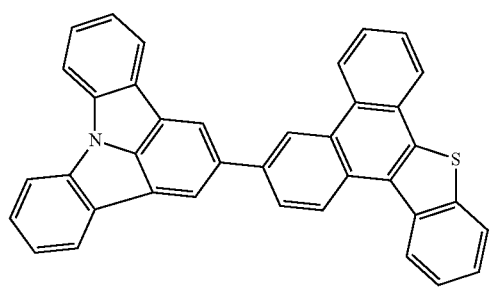
2-11
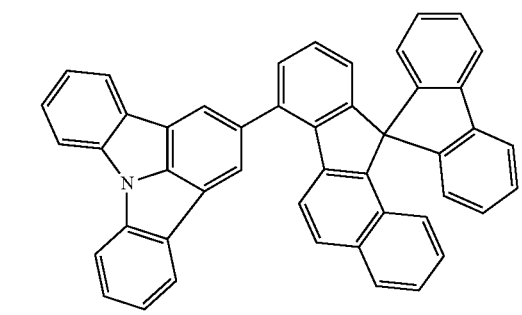
2-17
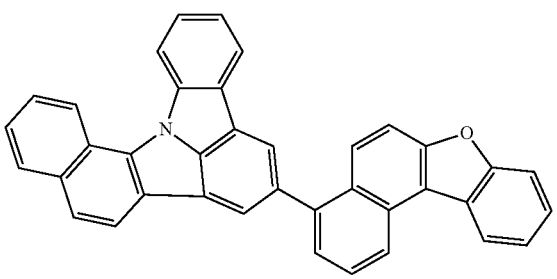
2-12
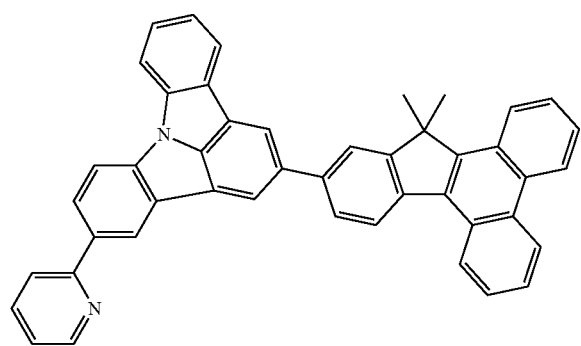
2-18
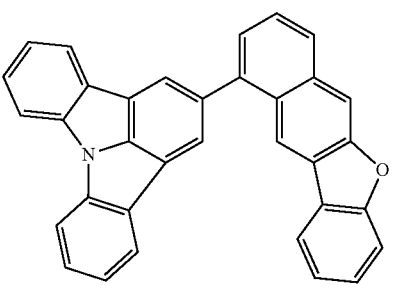

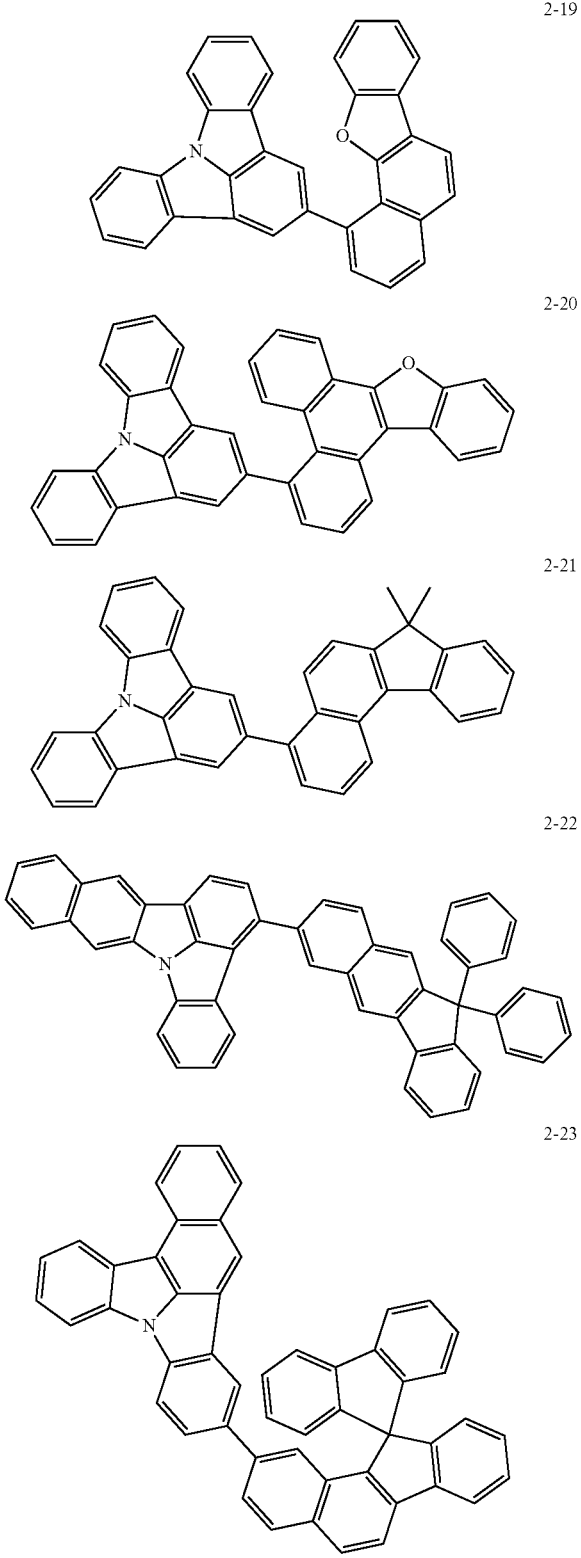

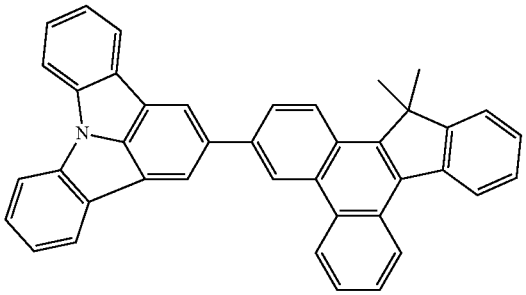

3. An organic electric element comprising a compound of claim 1.

4. The organic electric element of claim 3, comprising a first electrode; a second electrode; and an organic material layer positioned between the first electrode and the second electrode and including the compound; wherein the compound is a single compound or a mixture of two or more compounds.

5. The organic electric element of claim 3, further comprising a light efficiency enhancing layer formed on the side of the first electrode and/or the side of the second electrode facing the organic material layer.

6. The organic electric element of claim 3, wherein the organic material layer is formed by a spin coating process, a nozzle printing process, an inkjet printing process, a slot coating process, a dip coating process, or a roll-to-roll process.

7. The organic electric element of claim 3, wherein the organic material layer is an emitting layer.

8. An electronic device comprising the display device comprising the organic electric element of claim 3; and a control part driving the display device.

9. The electronic device according to claim 8, wherein the organic electric element is selected from the group consisting of an OLED, an organic solar cell, an organic photo conductor(OPC), Organic transistor(organic TFT) and an element for monochromic or white illumination.

10. An organic electric element comprising a compound of claim 2.

11. An electronic device comprising the display device comprising the organic electric element of claim 10; and a control part driving the display device.

* * * * *